United States Patent
Emery et al.

(10) Patent No.: US 10,085,783 B2
(45) Date of Patent: Oct. 2, 2018

(54) DEVICES AND METHODS FOR TREATING BONE TISSUE

(71) Applicant: IZI Medical Products, LLC, Owens Mills, MD (US)

(72) Inventors: Jeffrey L. Emery, Emerald Hills, CA (US); Laurent Schaller, Los Altos, CA (US); Ryan J. Connolly, Redwood City, CA (US); Andrew Huffmaster, Newark, CA (US); Ebrahim M. Quddus, Fremont, CA (US); Timothy J. McGrath, Fremont, CA (US); Sean M. Tutton, Shorewood, WI (US)

(73) Assignee: IZI MEDICAL PRODUCTS, LLC, Owens Mills, MD (US)

( * ) Notice: Subject to any disclaimer, the term of this patent is extended or adjusted under 35 U.S.C. 154(b) by 731 days.

(21) Appl. No.: 13/828,151

(22) Filed: Mar. 14, 2013

(65) Prior Publication Data

US 2014/0276471 A1    Sep. 18, 2014

(51) Int. Cl.
*A61B 17/88* (2006.01)
*A61B 17/34* (2006.01)
*A61B 17/00* (2006.01)

(52) U.S. Cl.
CPC ...... *A61B 17/8822* (2013.01); *A61B 17/8811* (2013.01); *A61B 17/3478* (2013.01); *A61B 2017/00331* (2013.01)

(58) Field of Classification Search
CPC ............ A61B 17/8819; A61B 17/8805; A61B 17/8811; A61B 17/8816; A61B 2017/3409; A61B 17/3472; A61B 2017/3443; A61B 2017/3445; A61B 17/7094; A61B 17/7097; A61M 25/0084; A61M 2025/0085; A61M 2025/0086; A61M 2025/0087;

(Continued)

(56) References Cited

U.S. PATENT DOCUMENTS

| 1,965,653 A | 7/1934 | Kennedy |
| 3,091,237 A | 5/1963 | Skinner |

(Continued)

FOREIGN PATENT DOCUMENTS

| DE | 197 10 392 | 7/1999 |
| DE | 19710392 C1 | 7/1999 |

(Continued)

OTHER PUBLICATIONS

US 5,669,928, 09/1997, Aust et al. (withdrawn)
(Continued)

*Primary Examiner* — Bhisma Mehta
*Assistant Examiner* — Laura Schell
(74) *Attorney, Agent, or Firm* — Ajay A. Jagtiani; Miles & Stockbridge P.C.

(57) ABSTRACT

The present disclosure relates to devices for injecting material into a body. The devices include a housing having a deployment cannula extending therefrom. The device also includes a rotary drive member wherein rotational movement of the drive member relative to the housing results in linear movement of an elongated injection member within a lumen of and out of a distal end opening of the deployment cannula. The elongated injection member includes a proximal end portion that may have a Tuohy-Huber tip and/or varying radii therealong.

19 Claims, 7 Drawing Sheets

(58) Field of Classification Search
CPC .... A61M 2025/0089; A61M 2025/009; A61M 2025/0091; A61M 2025/0092; A61M 2039/1033
See application file for complete search history.

(56) References Cited

U.S. PATENT DOCUMENTS

| | | |
|---|---|---|
| 3,112,743 A | 12/1963 | Cochran et al. |
| 3,648,294 A | 3/1972 | Shahrestani |
| 3,800,788 A | 4/1974 | White |
| 3,867,728 A | 2/1975 | Stubstad et al. |
| 3,875,595 A | 4/1975 | Froning |
| 3,889,685 A | 6/1975 | Ling et al. |
| 3,964,480 A | 6/1976 | Fronlng |
| 4,262,676 A | 4/1981 | Jamshidi |
| 4,274,183 A | 8/1981 | Malcom et al. |
| 4,312,337 A | 1/1982 | Donohue |
| 4,313,434 A | 2/1982 | Segal |
| 4,399,814 A | 8/1983 | Pratt, Jr. et al. |
| 4,462,394 A | 7/1984 | Jacobs |
| 4,458,435 A | 8/1984 | Murray |
| 4,487,479 A | 8/1984 | Brody |
| 4,488,549 A | 12/1984 | Lee et al. |
| 4,562,598 A | 1/1986 | Kranz |
| 4,595,006 A | 6/1986 | Burke et al. |
| 4,625,722 A | 12/1986 | Murray |
| 4,627,434 A | 12/1986 | Murray |
| 4,628,945 A | 12/1986 | Johnson, Jr. |
| 4,630,616 A | 12/1986 | Tretinyak |
| 4,665,906 A | 5/1987 | Jervis |
| 4,686,973 A | 8/1987 | Frisch |
| 4,697,584 A | 10/1987 | Haynes |
| 4,706,670 A | 11/1987 | Andersen et al. |
| 4,714,478 A | 12/1987 | Fischer |
| 4,743,256 A | 5/1988 | Brantigan |
| 4,772,287 A | 9/1988 | Ray et al. |
| 4,834,069 A | 5/1989 | Umeda |
| 4,838,282 A | 6/1989 | Strasser et al. |
| 4,863,476 A | 9/1989 | Shepperd |
| 4,878,915 A | 11/1989 | Brantigan |
| 4,888,022 A | 12/1989 | Huebsch |
| 4,888,024 A | 12/1989 | Powlan |
| 4,892,550 A | 1/1990 | Huebsch |
| 4,896,662 A | 1/1990 | Noble |
| 4,898,577 A | 2/1990 | Badger et al. |
| 4,904,261 A | 2/1990 | Dove et al. |
| 4,941,466 A | 7/1990 | Romano |
| 4,961,740 A | 10/1990 | Ray et al. |
| 4,969,888 A | 11/1990 | Scholten et al. |
| 5,015,247 A | 5/1991 | Michelson |
| 5,015,255 A | 5/1991 | Kusllch |
| 5,051,189 A | 9/1991 | Farrah |
| 5,053,035 A | 10/1991 | McLaren |
| 5,055,104 A | 10/1991 | Ray |
| 5,059,193 A | 10/1991 | Kuslich |
| 5,071,435 A | 12/1991 | Fuchs et al. |
| 5,098,435 A | 3/1992 | Stednitz et al. |
| 5,102,413 A | 4/1992 | Poddar |
| 5,108,404 A | 4/1992 | Scholten et al. |
| 5,119,044 A | 6/1992 | Hoedlmayr et al. |
| 5,122,130 A | 6/1992 | Keller |
| 5,123,926 A | 6/1992 | Pisharodi |
| 5,147,365 A | 9/1992 | Arroyo et al. |
| 5,163,989 A | 11/1992 | Campbell et al. |
| 5,171,280 A | 12/1992 | Baumgartner |
| 5,176,663 A | 1/1993 | Kimsey et al. |
| 5,176,692 A | 1/1993 | Wilk et al. |
| 5,183,052 A | 2/1993 | Terwilliger |
| 5,192,327 A | 3/1993 | Brantigan |
| 5,228,441 A | 7/1993 | Lundquist |
| 5,242,448 A | 9/1993 | Pettine et al. |
| 5,242,879 A | 9/1993 | Abe et al. |
| 5,257,632 A | 11/1993 | Turkel et al. |
| 5,263,953 A | 11/1993 | Bagby |
| 5,285,795 A | 2/1994 | Ryan et al. |
| 5,303,718 A | 4/1994 | Krajicek |
| 5,306,308 A | 4/1994 | Gross et al. |
| 5,306,310 A | 4/1994 | Siebels |
| 5,322,505 A | 6/1994 | Krause et al. |
| 5,330,429 A | 7/1994 | Noguchi et al. |
| 5,331,975 A | 7/1994 | Bonutti |
| 5,361,752 A | 11/1994 | Moll et al. |
| 5,383,932 A | 1/1995 | Wilson et al. |
| 5,385,151 A | 1/1995 | Scarfone et al. |
| 5,423,816 A | 6/1995 | Lin |
| 5,423,817 A | 6/1995 | Lin |
| 5,423,850 A | 6/1995 | Berger |
| 5,431,658 A | 7/1995 | Moskovich |
| 5,441,538 A | 8/1995 | Bonutti |
| 5,454,365 A | 10/1995 | Bonutti |
| 5,454,827 A | 10/1995 | Aust et al. |
| 5,456,686 A | 10/1995 | Klapper |
| 5,462,563 A | 10/1995 | Shearer et al. |
| 5,468,245 A | 11/1995 | Vargas, III |
| 5,480,400 A | 1/1996 | Berger |
| 5,484,437 A | 1/1996 | Michelson |
| 5,509,923 A | 4/1996 | Middleman et al. |
| 5,514,143 A | 5/1996 | Bonutti et al. |
| 5,514,153 A | 6/1996 | Bonutti |
| 5,522,398 A | 6/1996 | Goldenberg et al. |
| 5,522,790 A | 6/1996 | Moll et al. |
| 5,522,848 A | 6/1996 | Bonutti |
| 5,527,343 A | 6/1996 | Bonutti |
| 5,527,624 A | 6/1996 | Higgins et al. |
| 5,531,856 A | 7/1996 | Moll et al. |
| 5,534,023 A | 7/1996 | Henley |
| 5,538,009 A | 7/1996 | Byrne et al. |
| 5,540,711 A | 7/1996 | Kieturakis et al. |
| 5,545,222 A | 8/1996 | Bonutti |
| 5,549,679 A | 8/1996 | Kuslich |
| 5,562,736 A | 10/1996 | Ray et al. |
| 5,571,109 A | 11/1996 | Bertagnoli |
| 5,571,189 A | 11/1996 | Kuslich |
| 5,571,190 A | 11/1996 | Ulrich et al. |
| 5,575,790 A | 11/1996 | Chen et al. |
| 5,593,409 A | 1/1997 | Michelson |
| 5,601,556 A | 2/1997 | Pisharodi |
| 5,601,572 A | 2/1997 | Middleman et al. |
| 5,632,746 A | 5/1997 | Middleman et al. |
| 5,645,597 A | 7/1997 | Krapiva |
| 5,665,122 A | 9/1997 | Karabin |
| 5,674,295 A | 10/1997 | Ray et al. |
| 5,681,263 A | 10/1997 | Flesch |
| 5,693,100 A | 12/1997 | Pisharodi |
| 5,695,513 A | 12/1997 | Johnson et al. |
| 5,700,239 A | 12/1997 | Yoon |
| 5,702,453 A | 12/1997 | Rabbe et al. |
| 5,702,454 A | 12/1997 | Baumgartner |
| 5,716,416 A | 2/1998 | Lin |
| 5,741,253 A | 4/1998 | Michelson |
| 5,749,679 A | 5/1998 | Middleman et al. |
| 5,755,797 A | 5/1998 | Baumgartner |
| 5,756,127 A | 5/1998 | Grisoni et al. |
| 5,766,252 A | 6/1998 | Henry |
| 5,772,661 A | 6/1998 | Michelson |
| 5,782,832 A | 7/1998 | Larsen et al. |
| 5,788,703 A | 8/1998 | Mittelmeier et al. |
| 5,807,275 A | 9/1998 | Jamshidi |
| 5,820,628 A | 10/1998 | Middleman et al. |
| 5,823,979 A | 10/1998 | Mezo |
| 5,824,093 A | 10/1998 | Ray et al. |
| 5,827,289 A | 10/1998 | Reiley et al. |
| 5,836,948 A | 11/1998 | Zucherman et al. |
| 5,843,017 A * | 12/1998 | Yoon ........................... 600/564 |
| 5,848,986 A | 12/1998 | Lundquist et al. |
| 5,851,212 A | 12/1998 | Zirps et al. |
| 5,860,977 A | 1/1999 | Zucherman et al. |
| 5,865,848 A | 2/1999 | Baker |
| 5,871,470 A * | 2/1999 | McWha ............. A61B 17/3401 604/158 |
| 5,904,690 A | 5/1999 | Middleman et al. |
| 5,919,235 A | 7/1999 | Husson |
| 5,925,074 A | 7/1999 | Gingras et al. |
| 5,961,554 A | 10/1999 | Janson et al. |

(56) References Cited

U.S. PATENT DOCUMENTS

| | | |
|---|---|---|
| 5,972,015 A | 10/1999 | Scribner et al. |
| 5,976,186 A | 11/1999 | Bao et al. |
| 5,980,522 A | 11/1999 | Koros et al. |
| 6,012,494 A | 1/2000 | Balazs |
| 6,015,436 A | 1/2000 | Schonhoffer |
| 6,019,793 A | 2/2000 | Perren et al. |
| 6,030,401 A | 2/2000 | Marino |
| 6,033,406 A | 3/2000 | Mathews |
| 6,033,412 A | 3/2000 | Losken et al. |
| 6,039,740 A | 3/2000 | Olerud |
| 6,039,761 A | 3/2000 | Li |
| 6,045,552 A | 4/2000 | Zucherman et al. |
| 6,048,342 A | 4/2000 | Zucherman et al. |
| 6,048,346 A | 4/2000 | Reiley et al. |
| 6,048,360 A | 4/2000 | Khosravi et al. |
| 6,066,154 A | 5/2000 | Reiley et al. |
| 6,068,630 A | 5/2000 | Zucherman et al. |
| 6,073,051 A | 6/2000 | Sharkey et al. |
| 6,083,226 A | 7/2000 | Winslow et al. |
| 6,090,143 A | 7/2000 | Meriwether et al. |
| 6,096,080 A | 8/2000 | Nicholson |
| 6,102,950 A | 8/2000 | Vaccaro |
| 6,110,210 A | 8/2000 | Norton et al. |
| 6,113,640 A | 9/2000 | Tormala et al. |
| 6,123,705 A | 9/2000 | Michelson |
| 6,126,660 A | 10/2000 | Dietz |
| 6,127,597 A | 10/2000 | Beyar et al. |
| 6,159,211 A | 12/2000 | Boriani et al. |
| 6,159,244 A | 12/2000 | Suddaby |
| 6,165,218 A | 12/2000 | Husson et al. |
| 6,174,337 B1 | 1/2001 | Keenan |
| 6,179,873 B1 | 1/2001 | Zientek |
| 6,187,048 B1 | 2/2001 | Milner et al. |
| 6,190,414 B1 | 2/2001 | Young et al. |
| 6,193,757 B1 | 2/2001 | Foley et al. |
| 6,197,033 B1 | 3/2001 | Hald, Jr. et al. |
| D439,980 S | 4/2001 | Reiley et al. |
| 6,217,579 B1 | 4/2001 | Koros |
| 6,221,082 B1 | 4/2001 | Marino et al. |
| 6,224,603 B1 | 5/2001 | Marino |
| 6,235,030 B1 | 5/2001 | Zucherman et al. |
| 6,235,043 B1 | 5/2001 | Reiley et al. |
| 6,238,491 B1 | 5/2001 | Davidson et al. |
| 6,241,734 B1 | 6/2001 | Scribner et al. |
| 6,248,110 B1 | 6/2001 | Reiley et al. |
| 6,251,140 B1 | 6/2001 | Marino et al. |
| 6,261,289 B1 | 7/2001 | Levy |
| 6,261,763 B1 | 7/2001 | Castro |
| 6,264,695 B1 | 7/2001 | Stoy |
| 6,280,456 B1 | 8/2001 | Scribner et al. |
| 6,280,475 B1 | 8/2001 | Bao et al. |
| 6,290,724 B1 | 9/2001 | Marino |
| D449,691 S | 10/2001 | Relley et al. |
| 6,296,647 B1 | 10/2001 | Robioneck et al. |
| 6,312,443 B1 | 11/2001 | Stone |
| 6,364,828 B1 | 4/2002 | Yeung et al. |
| 6,368,325 B1 | 4/2002 | McKinley et al. |
| 6,387,130 B1 | 5/2002 | Stone et al. |
| 6,402,750 B1 | 6/2002 | Atkinson et al. |
| 6,419,641 B1 | 7/2002 | Mark et al. |
| 6,419,705 B1 | 7/2002 | Erickson |
| 6,423,071 B1 | 7/2002 | Lawson |
| 6,423,083 B2 | 7/2002 | Reiley et al. |
| 6,423,089 B1 | 7/2002 | Gingras et al. |
| 6,425,887 B1 | 7/2002 | McGuckin et al. |
| 6,425,919 B1 | 7/2002 | Lambrecht |
| 6,428,541 B1 | 8/2002 | Boyd et al. |
| 6,436,140 B1 | 8/2002 | Liu et al. |
| 6,440,138 B1 | 8/2002 | Reiley et al. |
| 6,451,019 B1 | 9/2002 | Zucherman et al. |
| 6,468,279 B1 | 10/2002 | Reo |
| 6,432,235 B1 | 11/2002 | Lambrecht et al. |
| 6,478,805 B1 | 11/2002 | Marino et al. |
| 6,485,518 B1 | 11/2002 | Cornwall et al. |
| D467,657 S | 12/2002 | Scribner |
| 6,488,710 B2 | 12/2002 | Besselink |
| 6,491,626 B1 | 12/2002 | Stone et al. |
| 6,491,695 B1 | 12/2002 | Roggenbuck |
| 6,491,826 B1 | 12/2002 | Stone et al. |
| 6,498,421 B1 | 12/2002 | Oh |
| 6,500,178 B2 | 12/2002 | Zucherman et al. |
| 6,500,205 B1 | 12/2002 | Michelson |
| 6,508,839 B1 | 1/2003 | Lambrecht et al. |
| 6,511,471 B2 | 1/2003 | Rosenman et al. |
| 6,612,958 B2 | 1/2003 | Swoyer et al. |
| D469,871 S | 2/2003 | Sand |
| 6,520,991 B2 | 2/2003 | Huene |
| D472,323 S | 3/2003 | Sand |
| 6,530,930 B1 | 3/2003 | Marino et al. |
| 6,533,791 B1 | 3/2003 | Betz et al. |
| 6,533,797 B1 | 3/2003 | Stone et al. |
| 6,540,747 B1 | 4/2003 | Marino |
| 6,554,833 B2 | 4/2003 | Levy et al. |
| 6,558,390 B2 | 5/2003 | Cragg |
| 6,562,074 B2 | 5/2003 | Gerbec et al. |
| 6,572,593 B1 | 6/2003 | Daum |
| 6,575,919 B1 | 6/2003 | Reiley et al. |
| 6,575,979 B1 | 6/2003 | Cragg |
| 6,576,016 B1 | 6/2003 | Hochshuler et al. |
| 6,579,291 B1 | 6/2003 | Keith et al. |
| 6,582,431 B1 | 6/2003 | Ray |
| 6,582,433 B2 | 6/2003 | Yun |
| 6,592,559 B1 | 7/2003 | Pakter et al. |
| 6,595,998 B2 | 7/2003 | Johnson et al. |
| 6,602,293 B1 | 8/2003 | Biermann et al. |
| 6,607,530 B1 | 8/2003 | Carl et al. |
| 6,607,544 B1 | 8/2003 | Boucher et al. |
| 6,610,094 B2 | 8/2003 | Husson |
| 6,613,054 B2 | 9/2003 | Scribner et al. |
| 6,620,190 B1 | 9/2003 | Trieu |
| 6,620,196 B1 | 9/2003 | Trieu |
| 6,623,505 B2 | 9/2003 | Scribner et al. |
| D482,787 S | 11/2003 | Reiss |
| 6,641,587 B2 | 11/2003 | Scribner et al. |
| 6,645,213 B2 | 11/2003 | Sand et al. |
| 6,648,917 B2 | 11/2003 | Gerbec et al. |
| D483,495 S | 12/2003 | Sand |
| 6,656,178 B1 | 12/2003 | Veidhuizen et al. |
| 6,656,180 B2 | 12/2003 | Stahurski |
| 6,660,037 B1 | 12/2003 | Husson et al. |
| 6,663,647 B2 | 12/2003 | Reiley et al. |
| 6,666,890 B2 | 12/2003 | Michelson |
| 6,666,891 B2 | 12/2003 | Boehm, Jr. et al. |
| 6,676,663 B2 | 1/2004 | Higueras et al. |
| 6,676,665 B2 | 1/2004 | Foley et al. |
| 6,682,561 B2 | 1/2004 | Songer et al. |
| 6,685,742 B1 | 2/2004 | Jackson |
| 6,689,125 B1 | 2/2004 | Keith et al. |
| 6,689,168 B2 | 2/2004 | Lleberman |
| 6,692,563 B2 | 2/2004 | Zimmermann |
| 6,706,070 B1 | 3/2004 | Wagner et al. |
| 6,710,216 B1 | 4/2004 | Boucher et al. |
| 6,716,247 B2 | 4/2004 | Michelson |
| 6,716,957 B2 | 4/2004 | Tunc |
| 6,719,761 B1 | 4/2004 | Reiley et al. |
| 6,719,773 B1 | 4/2004 | Boucher et al. |
| 6,723,128 B2 | 4/2004 | Uk |
| 6,726,691 B2 | 4/2004 | Osorio et al. |
| D490,159 S | 5/2004 | Sand |
| 6,740,093 B2 | 5/2004 | Hochschuler et al. |
| D492,032 S | 6/2004 | Muller et al. |
| 6,749,560 B1 | 6/2004 | Konstorum et al. |
| 6,755,841 B2 | 6/2004 | Fraser et al. |
| D492,775 S | 7/2004 | Doelling et al. |
| D493,533 S | 7/2004 | Blain |
| 6,758,673 B2 | 7/2004 | Fromovich et al. |
| 6,764,514 B1 | 7/2004 | Li et al. |
| D495,417 S | 8/2004 | Doelling et al. |
| 6,773,460 B2 | 8/2004 | Jackson |
| 6,780,151 B2 | 8/2004 | Grabover et al. |
| 6,783,530 B1 | 8/2004 | Levy |
| 6,793,679 B2 | 9/2004 | Michelson |
| 6,796,983 B1 | 9/2004 | Zucherman et al. |
| 6,805,695 B2 | 10/2004 | Keith et al. |

(56) References Cited

U.S. PATENT DOCUMENTS

| | | | |
|---|---|---|---|
| 6,805,697 B1 | 10/2004 | Helm et al. |
| 6,808,537 B2 | 10/2004 | Michelson |
| 6,814,736 B2 | 11/2004 | Reiley et al. |
| 6,814,756 B1 | 11/2004 | Michelson |
| 6,821,298 B1 | 11/2004 | Jackson |
| 6,830,589 B2 | 12/2004 | Erickson |
| 6,835,205 B2 | 12/2004 | Atkinson et al. |
| 6,835,206 B2 | 12/2004 | Jackson |
| 6,840,944 B2 | 1/2005 | Suddaby |
| 6,852,126 B2 | 2/2005 | Ahlgren |
| 6,852,129 B2 | 2/2005 | Gerbec et al. |
| 6,863,668 B2 | 3/2005 | Gillespie et al. |
| 6,863,672 B2 | 3/2005 | Reiley et al. |
| 6,863,673 B2 | 3/2005 | Gerbec et al. |
| 6,866,682 B1 | 3/2005 | An et al. |
| 6,875,219 B2 | 4/2005 | Arramon et al. |
| 6,881,228 B2 | 4/2005 | Zdeblick et al. |
| 6,883,520 B2 | 4/2005 | Lambrecht et al. |
| 6,887,248 B2 | 5/2005 | McKinley et al. |
| 6,893,466 B2 | 5/2005 | Trieu |
| 6,899,716 B2 | 5/2005 | Cragg |
| 6,899,719 B2 | 5/2005 | Reiley et al. |
| D506,828 S | 6/2005 | Layne et al. |
| 6,905,512 B2 | 6/2005 | Paes et al. |
| 6,908,506 B2 | 6/2005 | Zimmermann |
| 6,921,403 B2 | 7/2005 | Cragg et al. |
| 6,923,810 B1 | 8/2005 | Michelson |
| 6,923,813 B2 | 8/2005 | Phillips et al. |
| 6,923,814 B1 | 8/2005 | Hildebrand et al. |
| 6,929,647 B2 | 8/2005 | Cohen |
| 6,946,973 B1 | 9/2005 | Bray |
| 6,952,129 B2 | 10/2005 | Lin et al. |
| 6,962,606 B2 | 11/2005 | Michelson |
| 6,964,674 B1 | 11/2005 | Matsuura et al. |
| D512,506 S | 12/2005 | Layne et al. |
| 6,972,035 B2 | 12/2005 | Michelson |
| 6,974,479 B2 | 12/2005 | Trieu |
| 6,979,341 B2 | 12/2005 | Scribner et al. |
| 6,981,981 B2 | 1/2006 | Reiley et al. |
| 6,997,929 B2 | 2/2006 | Manzi et al. |
| 7,004,945 B2 | 2/2006 | Boyd et al. |
| 7,008,453 B1 | 3/2006 | Michelson |
| 7,014,633 B2 | 3/2006 | Cragg |
| 7,018,089 B2 | 3/2006 | Wenz et al. |
| 7,018,415 B1 | 3/2006 | McKay |
| 7,018,453 B2 | 3/2006 | Klein et al. |
| 7,029,498 B2 | 4/2006 | Boehm et al. |
| 7,044,954 B2 | 5/2006 | Relley et al. |
| 7,048,694 B2 | 5/2006 | Mark et al. |
| 7,063,703 B2 | 6/2006 | Reo |
| 7,066,961 B2 | 6/2006 | Michelson |
| 7,069,087 B2 | 6/2006 | Sharkey et al. |
| 7,070,598 B2 | 7/2006 | Lim et al. |
| 7,074,226 B2 | 7/2006 | Roehm, III et al. |
| 7,081,120 B2 | 7/2006 | Li et al. |
| 7,081,122 B1 | 7/2006 | Reiley et al. |
| 7,087,055 B2 | 8/2006 | Lim et al. |
| 7,094,257 B2 | 8/2006 | Mujwid et al. |
| 7,115,128 B2 | 10/2006 | Michelson |
| 7,115,163 B2 | 10/2006 | Zimmermann |
| 7,118,579 B2 | 10/2006 | Michelson |
| 7,118,580 B1 | 10/2006 | Beyersdorff et al. |
| 7,118,598 B2 | 10/2006 | Michelson |
| 7,124,761 B2 | 10/2006 | Lambrecht et al. |
| 7,128,760 B2 | 10/2006 | Michelson |
| 7,135,424 B2 | 11/2006 | Worley et al. |
| 7,153,304 B2 | 12/2006 | Robie et al. |
| 7,153,305 B2 | 12/2006 | Johnson |
| 7,153,306 B2 | 12/2006 | Ralph et al. |
| 7,153,307 B2 | 12/2006 | Scribner et al. |
| 7,156,874 B2 | 1/2007 | Paponneau et al. |
| 7,156,875 B2 | 1/2007 | Michelson |
| 7,166,107 B2 | 1/2007 | Anderson |
| 7,179,293 B2 | 2/2007 | McKay |
| 7,189,242 B2 | 3/2007 | Boyd et al. |
| 7,204,851 B2 | 4/2007 | Trieu et al. |
| 7,207,991 B2 | 4/2007 | Michelson |
| 7,211,112 B2 | 5/2007 | Baynham et al. |
| 7,214,227 B2 | 5/2007 | Colleran et al. |
| 7,220,281 B2 | 5/2007 | Lambrecht et al. |
| 7,223,227 B2 | 5/2007 | Pflueger |
| 7,226,481 B2 | 6/2007 | Kuslich |
| 7,241,297 B2 | 7/2007 | Shaolian et al. |
| 7,244,273 B2 | 7/2007 | Pedersen et al. |
| 7,250,060 B2 | 7/2007 | Trieu |
| 7,242,671 B2 | 8/2007 | Scribner et al. |
| 7,267,687 B2 | 9/2007 | McGuckin |
| 7,270,679 B2 | 9/2007 | Istephanous et al. |
| 7,276,062 B2 | 10/2007 | McDaniel et al. |
| 7,311,713 B2 | 12/2007 | Johnson et al. |
| 7,316,679 B2 * | 1/2008 | Bierman ............... A61M 39/10 128/DIG. 26 |
| 7,316,714 B2 | 1/2008 | Gordon et al. |
| 7,318,840 B2 | 1/2008 | McKay |
| 7,320,689 B2 | 1/2008 | Keller |
| 7,322,962 B2 | 1/2008 | Forrest |
| 7,383,639 B2 | 6/2008 | Malandain |
| 7,485,134 B2 | 2/2009 | Simonson |
| 7,608,083 B2 | 10/2009 | Lee et al. |
| 7,637,905 B2 | 12/2009 | Saadat et al. |
| 7,713,273 B2 | 5/2010 | Krueger et al. |
| 7,799,035 B2 | 9/2010 | Krueger et al. |
| 7,828,807 B2 | 11/2010 | LeHuec et al. |
| 8,057,544 B2 | 11/2011 | Schaller |
| 8,128,633 B2 | 3/2012 | Linderman et al. |
| 8,187,327 B2 | 5/2012 | Edldin et al. |
| 8,236,029 B2 | 8/2012 | Siegal |
| D669,168 S | 10/2012 | Krueger et al. |
| 8,529,576 B2 | 9/2013 | Krueger et al. |
| 2001/0011174 A1 | 8/2001 | Reiley et al. |
| 2001/0016741 A1 | 8/2001 | Burkus et al. |
| 2001/0049531 A1 | 12/2001 | Reiley |
| 2002/0016583 A1 | 2/2002 | Cragg |
| 2002/0026195 A1 | 2/2002 | Layne et al. |
| 2002/0026244 A1 | 2/2002 | Trieu |
| 2002/0045942 A1 | 4/2002 | Ham |
| 2002/0068974 A1 | 6/2002 | Kuslich et al. |
| 2002/0077700 A1 | 6/2002 | Varga et al. |
| 2002/0082584 A1 | 6/2002 | Rosenman et al. |
| 2002/0082608 A1 | 6/2002 | Reiley et al. |
| 2002/0087163 A1 | 7/2002 | Dixon et al. |
| 2002/0091390 A1 | 7/2002 | Michelson |
| 2002/0099385 A1 | 7/2002 | Ralph et al. |
| 2002/0107519 A1 | 8/2002 | Dixon et al. |
| 2002/0107573 A1 | 8/2002 | Steinberg |
| 2002/0120238 A1 * | 8/2002 | McGuckin, Jr. ....... A61B 18/00 604/187 |
| 2002/0156482 A1 | 10/2002 | Scribner et al. |
| 2002/0169471 A1 | 11/2002 | Ferdinand |
| 2002/0172851 A1 | 11/2002 | Corey et al. |
| 2002/0173796 A1 | 11/2002 | Cragg |
| 2002/0173841 A1 | 11/2002 | Ortiz et al. |
| 2002/0173851 A1 | 11/2002 | McKay |
| 2002/0183761 A1 | 12/2002 | Johnson |
| 2002/0183778 A1 | 12/2002 | Relley et al. |
| 2002/0191457 A1 | 12/2002 | Sand |
| 2003/0018390 A1 | 1/2003 | Husson |
| 2003/0032963 A1 | 2/2003 | Reiss et al. |
| 2003/0050644 A1 | 3/2003 | Boucher et al. |
| 2003/0069593 A1 | 4/2003 | Tremulls et al. |
| 2003/0074075 A1 | 4/2003 | Thomas, Jr. |
| 2003/0108588 A1 | 6/2003 | Chen et al. |
| 2003/0130664 A1 | 7/2003 | Boucher |
| 2003/0171812 A1 | 9/2003 | Grunberg et al. |
| 2003/0191414 A1 | 10/2003 | Reiley et al. |
| 2003/0191489 A1 | 10/2003 | Reiley et al. |
| 2003/0195518 A1 | 10/2003 | Cragg |
| 2003/0195547 A1 | 10/2003 | Scribner et al. |
| 2003/0195630 A1 | 10/2003 | Ferree |
| 2003/0199979 A1 | 10/2003 | McGuckin, Jr. |
| 2003/0203136 A1 | 10/2003 | Takeuchi |
| 2003/0220648 A1 | 11/2003 | Osorio et al. |
| 2003/0220695 A1 | 11/2003 | Sevrain |
| 2003/0229372 A1 | 12/2003 | Reiley et al. |

(56) References Cited

U.S. PATENT DOCUMENTS

| | | |
|---|---|---|
| 2003/0233096 A1 | 12/2003 | Osorio et al. |
| 2003/0233146 A1 | 12/2003 | Grinberg |
| 2004/0010251 A1 | 1/2004 | Pitaru et al. |
| 2004/0010260 A1 | 1/2004 | Scribner et al. |
| 2004/0010263 A1 | 1/2004 | Boucher et al. |
| 2004/0019354 A1 | 1/2004 | Johnson et al. |
| 2004/0024408 A1 | 2/2004 | Burkus et al. |
| 2004/0024409 A1 | 2/2004 | Sand et al. |
| 2004/0024463 A1 | 2/2004 | Thomas, Jr. et al. |
| 2004/0024465 A1 | 2/2004 | Lambrecht et al. |
| 2004/0034343 A1 | 2/2004 | Gillespie et al. |
| 2004/0034429 A1 | 2/2004 | Lambrecht et al. |
| 2004/0049203 A1 | 3/2004 | Scribner et al. |
| 2004/0059333 A1 | 3/2004 | Carl |
| 2004/0059339 A1 | 3/2004 | Roehm, III et al. |
| 2004/0059418 A1 | 3/2004 | McKay et al. |
| 2004/0032953 A1 | 4/2004 | Petit |
| 2004/0064144 A1 | 4/2004 | Johnson |
| 2004/0073308 A1 | 4/2004 | Kusllch et al. |
| 2004/0087947 A1 | 5/2004 | Lim et al. |
| 2004/0092933 A1 | 5/2004 | Shaolian et al. |
| 2004/0092948 A1 | 5/2004 | Stevens et al. |
| 2004/0092988 A1 | 5/2004 | Shaolian et al. |
| 2004/0097924 A1 | 5/2004 | Lambrecht et al. |
| 2004/0097930 A1 | 5/2004 | Justis et al. |
| 2004/0097932 A1 | 5/2004 | Ray, III et al. |
| 2004/0098131 A1 | 5/2004 | Bryan et al. |
| 2004/0102774 A1 | 5/2004 | Trieu |
| 2004/0106940 A1 | 6/2004 | Shaolian et al. |
| 2004/0111161 A1 | 6/2004 | Trieu |
| 2004/0117019 A1 | 6/2004 | Trieu et al. |
| 2004/0133124 A1 | 7/2004 | Bates et al. |
| 2004/0133229 A1 | 7/2004 | Lambrecht et al. |
| 2004/0133280 A1 | 7/2004 | Trieu |
| 2004/0138748 A1 | 7/2004 | Boyer, II et al. |
| 2004/0153064 A1 | 8/2004 | Foley et al. |
| 2004/0153115 A1 | 8/2004 | Reiley et al. |
| 2004/0158206 A1 | 8/2004 | Aboul-Hosn et al. |
| 2004/0167561 A1 | 8/2004 | Boucher et al. |
| 2004/0167562 A1 | 8/2004 | Osorio et al. |
| 2004/0167625 A1 | 8/2004 | Beyar et al. |
| 2004/0176775 A1 | 9/2004 | Burkus et al. |
| 2004/0186471 A1 | 9/2004 | Trieu |
| 2004/0186528 A1 | 9/2004 | Ries et al. |
| 2004/0186573 A1 | 9/2004 | Ferree |
| 2004/0210231 A1 | 10/2004 | Boucher et al. |
| 2004/0210310 A1 | 10/2004 | Trieu |
| 2004/0215344 A1 | 10/2004 | Hochschuler et al. |
| 2004/0220580 A1 | 11/2004 | Johnson et al. |
| 2004/0220672 A1 | 11/2004 | Shadduck |
| 2004/0225296 A1 | 11/2004 | Reiss et al. |
| 2004/0225361 A1 | 11/2004 | Glenn |
| 2004/0230191 A1 | 11/2004 | Frey et al. |
| 2004/0230309 A1 | 11/2004 | DiMauro |
| 2004/0243229 A1 | 12/2004 | Vidlund et al. |
| 2004/0243241 A1 | 12/2004 | Istephanous |
| 2004/0249377 A1 | 12/2004 | Kaes et al. |
| 2004/0254520 A1 | 12/2004 | Porteous et al. |
| 2004/0254644 A1 | 12/2004 | Taylor |
| 2004/0260300 A1 | 12/2004 | Gorensek et al. |
| 2004/0260397 A1 | 12/2004 | Lambrecht et al. |
| 2004/0267271 A9 | 12/2004 | Scribner et al. |
| 2005/0004578 A1 | 1/2005 | Lambrecht et al. |
| 2005/0010293 A1 | 1/2005 | Zucherman et al. |
| 2005/0010298 A1 | 1/2005 | Zucherman et al. |
| 2005/0015148 A1 | 1/2005 | Jansen et al. |
| 2005/0015152 A1 | 1/2005 | Sweeney |
| 2005/0021041 A1 | 1/2005 | Michelson |
| 2005/0033295 A1 | 2/2005 | Wisnewski |
| 2005/0033440 A1 | 2/2005 | Lambrecht et al. |
| 2005/0038517 A1 | 2/2005 | Carrison |
| 2005/0043737 A1 | 2/2005 | Reiley et al. |
| 2005/0043796 A1 | 2/2005 | Grant et al. |
| 2005/0054948 A1 | 3/2005 | Goldenberg |
| 2005/0055097 A1 | 3/2005 | Grunberg et al. |
| 2005/0060036 A1 | 3/2005 | Schultz et al. |
| 2005/0060038 A1 | 3/2005 | Lambrecht et al. |
| 2005/0065519 A1 | 3/2005 | Michelson |
| 2005/0065609 A1 | 3/2005 | Wardlaw |
| 2005/0069571 A1 | 3/2005 | Slivka et al. |
| 2005/0070908 A1 | 3/2005 | Cragg |
| 2005/0070911 A1 | 3/2005 | Carrison |
| 2005/0070913 A1 | 3/2005 | Milbocker et al. |
| 2005/0071011 A1 | 3/2005 | Ralph et al. |
| 2005/0080488 A1 | 4/2005 | Schultz |
| 2005/0085912 A1 | 4/2005 | Amin et al. |
| 2005/0090833 A1 | 4/2005 | DiPoto |
| 2005/0090852 A1 | 4/2005 | Layne et al. |
| 2005/0090899 A1 | 4/2005 | DiPoto |
| 2005/0107880 A1 | 5/2005 | Shimp et al. |
| 2005/0113918 A1 | 5/2005 | Messerll et al. |
| 2005/0113919 A1 | 5/2005 | Cragg et al. |
| 2005/0113928 A1 | 5/2005 | Cragg et al. |
| 2005/0118228 A1 | 6/2005 | Trieu |
| 2005/0119662 A1 | 6/2005 | Reiley et al. |
| 2005/0119750 A1 | 6/2005 | Studer |
| 2005/0119751 A1 | 6/2005 | Lawson |
| 2005/0119752 A1 | 6/2005 | Williams et al. |
| 2005/0119754 A1 | 6/2005 | Trieu et al. |
| 2005/0124989 A1 | 6/2005 | Suddaby |
| 2005/0124992 A1 | 6/2005 | Ferree |
| 2005/0124999 A1 | 6/2005 | Teitelbaum et al. |
| 2005/0125002 A1* | 6/2005 | Baran ............... A61M 25/0041 606/108 |
| 2005/0125066 A1 | 6/2005 | McAfee |
| 2005/0131267 A1 | 6/2005 | Talmadge |
| 2005/0131268 A1 | 6/2005 | Talmadge |
| 2005/0131269 A1 | 6/2005 | Talmadge |
| 2005/0131536 A1 | 6/2005 | Eisermann et al. |
| 2005/0131540 A1 | 6/2005 | Trieu |
| 2005/0131541 A1 | 6/2005 | Trieu |
| 2005/0137602 A1 | 6/2005 | Assell et al. |
| 2005/0142211 A1 | 6/2005 | Wenz |
| 2005/0143763 A1 | 6/2005 | Ortiz et al. |
| 2005/0143827 A1 | 6/2005 | Globerman et al. |
| 2005/0149022 A1 | 7/2005 | Shaolian et al. |
| 2005/0149191 A1 | 7/2005 | Cragg et al. |
| 2005/0149194 A1 | 7/2005 | Ahlgren |
| 2005/0149197 A1 | 7/2005 | Cauthen |
| 2005/0154396 A1 | 7/2005 | Foley et al. |
| 2005/0154483 A1 | 7/2005 | Trieu |
| 2005/0165406 A1 | 7/2005 | Assell et al. |
| 2005/0171539 A1 | 8/2005 | Braun et al. |
| 2005/0171552 A1 | 8/2005 | Johnson et al. |
| 2005/0182412 A1 | 8/2005 | Johnson et al. |
| 2005/0182413 A1 | 8/2005 | Johnson et al. |
| 2005/0182414 A1 | 8/2005 | Manzi et al. |
| 2005/0187556 A1 | 8/2005 | Stack et al. |
| 2005/0187558 A1 | 8/2005 | Johnson et al. |
| 2005/0187559 A1 | 8/2005 | Raymond et al. |
| 2005/0187564 A1 | 8/2005 | Jayaraman |
| 2005/0197707 A1 | 9/2005 | Trieu et al. |
| 2005/0216018 A1 | 9/2005 | Sennett |
| 2005/0216087 A1 | 9/2005 | Zucherman et al. |
| 2005/0222684 A1 | 10/2005 | Ferree |
| 2005/0228383 A1 | 10/2005 | Zucherman et al. |
| 2005/0228391 A1 | 10/2005 | Levy et al. |
| 2005/0228397 A1 | 10/2005 | Malandain et al. |
| 2005/0234425 A1 | 10/2005 | Miller et al. |
| 2005/0234451 A1 | 10/2005 | Markworth |
| 2005/0234452 A1 | 10/2005 | Malandain |
| 2005/0234456 A1 | 10/2005 | Malandain |
| 2005/0240182 A1 | 10/2005 | Zucherman et al. |
| 2005/0240189 A1 | 10/2005 | Rousseau et al. |
| 2005/0240193 A1 | 10/2005 | Layne et al. |
| 2005/0240269 A1 | 10/2005 | Lambrecht et al. |
| 2005/0251149 A1 | 11/2005 | Wenz |
| 2005/0251260 A1 | 11/2005 | Gerber et al. |
| 2005/0261684 A1 | 11/2005 | Shaolian et al. |
| 2005/0261695 A1 | 11/2005 | Cragg et al. |
| 2005/0261781 A1 | 11/2005 | Sennett et al. |
| 2005/0267471 A1 | 12/2005 | Biedermann |
| 2005/0273166 A1 | 12/2005 | Sweeney |
| 2005/0273173 A1 | 12/2005 | Gordon |

(56) References Cited

U.S. PATENT DOCUMENTS

| | | |
|---|---|---|
| 2005/0278023 A1 | 12/2005 | Zwirkoskl |
| 2005/0278027 A1 | 12/2005 | Hyde, Jr |
| 2005/0278029 A1 | 12/2005 | Trieu |
| 2005/0283244 A1 | 12/2005 | Gordon et al. |
| 2005/0287071 A1 | 12/2005 | Wenz |
| 2006/0004456 A1 | 1/2006 | McKay |
| 2006/0009779 A1 | 1/2006 | Collins et al. |
| 2006/0030850 A1 | 2/2006 | Keegan et al. |
| 2006/0030933 A1 | 2/2006 | DeLegge |
| 2006/0030943 A1 | 2/2006 | Peterman |
| 2006/0036241 A1 | 2/2006 | Siegal |
| 2006/0036259 A1 | 2/2006 | Carl et al. |
| 2006/0036261 A1 | 2/2006 | McDonnell |
| 2006/0036273 A1 | 2/2006 | Siegal |
| 2006/0041258 A1 | 2/2006 | Galea |
| 2006/0045904 A1 | 3/2006 | Aronson |
| 2006/0058807 A1 | 3/2006 | Landry et al. |
| 2006/0058880 A1 | 3/2006 | Wysockl et al. |
| 2006/0064171 A1 | 3/2006 | Trieu |
| 2006/0069439 A1 | 3/2006 | Zucherman et al. |
| 2006/0085002 A1 | 4/2006 | Trieu et al. |
| 2006/0085009 A1 | 4/2006 | Truckai et al. |
| 2006/0089440 A1 | 4/2006 | Zucherman et al. |
| 2006/0089642 A1 | 4/2006 | Diaz et al. |
| 2006/0089646 A1 | 4/2006 | Bonutti |
| 2006/0089654 A1 | 4/2006 | Lins et al. |
| 2006/0089715 A1 | 4/2006 | Truckai et al. |
| 2006/0089718 A1 | 4/2006 | Zucherman et al. |
| 2006/0089719 A1 | 4/2006 | Trieu |
| 2006/0095045 A1 | 5/2006 | Trieu |
| 2006/0095046 A1 | 5/2006 | Trieu et al. |
| 2006/0095134 A1 | 5/2006 | Trieu et al. |
| 2006/0095138 A1 | 5/2006 | Truckai et al. |
| 2006/0100706 A1 | 5/2006 | Shadduck et al. |
| 2006/0106397 A1 | 5/2006 | Lins |
| 2006/0106459 A1 | 5/2006 | Truckal et al. |
| 2006/0122704 A1 | 6/2006 | Vresilovic et al. |
| 2006/0129244 A1 | 6/2006 | Ensign |
| 2006/0136064 A1 | 6/2006 | Sherman |
| 2006/0142858 A1 | 6/2006 | Colleran et al. |
| 2006/0142864 A1 | 6/2006 | Cauthen |
| 2006/0149136 A1 | 7/2006 | Seto et al. |
| 2006/0149237 A1 | 7/2006 | Markworth et al. |
| 2006/0149238 A1 | 7/2006 | Truckaie |
| 2006/0149252 A1 | 7/2006 | Markworth et al. |
| 2006/0149380 A1 | 7/2006 | Lotz et al. |
| 2006/0149397 A1 | 7/2006 | Kuslich et al. |
| 2006/0155379 A1 | 7/2006 | Heneveld, Sr. et al. |
| 2006/0161162 A1 | 7/2006 | Lambrecht et al. |
| 2006/0161166 A1 | 7/2006 | Johnson et al. |
| 2006/0167553 A1 | 7/2006 | Cauthen, III et al. |
| 2006/0173545 A1 | 8/2006 | Cauthen, III et al. |
| 2006/0178746 A1 | 8/2006 | Bartish, Jr. et al. |
| 2006/0184192 A1 | 8/2006 | Markworth et al. |
| 2006/0184247 A1 | 8/2006 | Edidin et al. |
| 2006/0184248 A1 | 8/2006 | Edidin et al. |
| 2006/0189999 A1 | 8/2006 | Zwirkoski |
| 2006/0190083 A1 | 8/2006 | Arnln et al. |
| 2006/0190085 A1 | 8/2006 | Cauthen |
| 2006/0195102 A1 | 8/2006 | Malandain |
| 2006/0195191 A1 | 8/2006 | Sweeney, II et al. |
| 2006/0200139 A1 | 9/2006 | Michelson |
| 2006/0200164 A1 | 9/2006 | Michelson |
| 2006/0200239 A1 | 9/2006 | Rothman et al. |
| 2006/0200240 A1 | 9/2006 | Rothman et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206116 A1 | 9/2006 | Yeung |
| 2006/0206207 A1 | 9/2006 | Dryer et al. |
| 2006/0235423 A1 | 10/2006 | Cantu |
| 2006/0235521 A1 | 10/2006 | Zucherman et al. |
| 2006/0241663 A1 | 10/2006 | Rice et al. |
| 2006/0241770 A1 | 10/2006 | Rhoda et al. |
| 2006/0247770 A1 | 11/2006 | Peterman |
| 2006/0247771 A1 | 11/2006 | Peterman et al. |
| 2006/0247781 A1 | 11/2006 | Francis |
| 2006/0264896 A1 | 11/2006 | Palmer |
| 2006/0264939 A1 | 11/2006 | Zucherman et al. |
| 2006/0264945 A1 | 11/2006 | Edidin et al. |
| 2006/0265067 A1 | 11/2006 | Zucherman et al. |
| 2006/0265077 A1 | 11/2006 | Zwirkoski |
| 2006/0271049 A1 | 11/2006 | Zucherman et al. |
| 2006/0271061 A1 | 11/2006 | Beyar et al. |
| 2006/0276897 A1 | 12/2006 | Winslow |
| 2006/0276899 A1 | 12/2006 | Zipnick et al. |
| 2006/0282167 A1 | 12/2006 | Lambrecht et al. |
| 2006/0287726 A1 | 12/2006 | Segal et al. |
| 2006/0287727 A1 | 12/2006 | Segal |
| 2006/0293662 A1 | 12/2006 | Boyer, II et al. |
| 2006/0293753 A1 | 12/2006 | Thramann |
| 2007/0006692 A1 | 1/2007 | Phan |
| 2007/0010716 A1 | 1/2007 | Malandain et al. |
| 2007/0010717 A1 | 1/2007 | Cragg |
| 2007/0010824 A1 | 1/2007 | Malandain et al. |
| 2007/0010844 A1 | 1/2007 | Gong et al. |
| 2007/0010845 A1 | 1/2007 | Gong et al. |
| 2007/0010846 A1 | 1/2007 | Leung et al. |
| 2007/0010848 A1 | 1/2007 | Leung et al. |
| 2007/0010889 A1 | 1/2007 | Francis |
| 2007/0032703 A1 | 2/2007 | Sankaran et al. |
| 2007/0032791 A1 | 2/2007 | Greenhalgh |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2007/0048382 A1 | 3/2007 | Meyer et al. |
| 2007/0049849 A1 | 3/2007 | Schwardt et al. |
| 2007/0049934 A1 | 3/2007 | Edidin et al. |
| 2007/0049935 A1 | 3/2007 | Edidin et al. |
| 2007/0050034 A1 | 3/2007 | Schwardt et al. |
| 2007/0050035 A1 | 3/2007 | Schwardt et al. |
| 2007/0055201 A1 | 3/2007 | Seto et al. |
| 2007/0055237 A1 | 3/2007 | Edidin et al. |
| 2007/0055246 A1 | 3/2007 | Zucherman et al. |
| 2007/0055265 A1 | 3/2007 | Schaller |
| 2007/0055266 A1 | 3/2007 | Osorio et al. |
| 2007/0055267 A1 | 3/2007 | Osorio et al. |
| 2007/0055271 A1 | 3/2007 | Schaller |
| 2007/0055272 A1 | 3/2007 | Schaller |
| 2007/0055273 A1 | 3/2007 | Schaller |
| 2007/0055274 A1 | 3/2007 | Appenzeller et al. |
| 2007/0055275 A1 | 3/2007 | Schaller |
| 2007/0055276 A1 | 3/2007 | Edidin |
| 2007/0055277 A1 | 3/2007 | Osorio et al. |
| 2007/0055278 A1 | 3/2007 | Osorio et al. |
| 2007/0055281 A1 | 3/2007 | Osorio et al. |
| 2007/0055284 A1 | 3/2007 | Osorio et al. |
| 2007/0055300 A1 | 3/2007 | Osorio et al. |
| 2007/0060933 A1 | 3/2007 | Sankaran et al. |
| 2007/0060935 A1 | 3/2007 | Schwardt et al. |
| 2007/0067034 A1 | 3/2007 | Chirico et al. |
| 2007/0068329 A1 | 3/2007 | Phan et al. |
| 2007/0073292 A1 | 3/2007 | Kohm et al. |
| 2007/0093689 A1 | 3/2007 | Steinberg |
| 2007/0093906 A1 | 3/2007 | Hudgins et al. |
| 2007/0078436 A1 | 4/2007 | Leung et al. |
| 2007/0078463 A1 | 4/2007 | Malandain |
| 2007/0093899 A1 | 4/2007 | Dutoit et al. |
| 2007/0123986 A1 | 5/2007 | Schaller |
| 2007/0135922 A1 | 6/2007 | Trieu |
| 2007/0149978 A1 | 6/2007 | Shezifi et al. |
| 2007/0150059 A1 | 6/2007 | Ruberte et al. |
| 2007/0150060 A1 | 6/2007 | Trieu |
| 2007/0150061 A1 | 6/2007 | Trieu |
| 2007/0150063 A1 | 6/2007 | Ruberte et al. |
| 2007/0150064 A1 | 6/2007 | Ruberte et al. |
| 2007/0162127 A1 | 7/2007 | Peterman et al. |
| 2007/0167945 A1 | 7/2007 | Lange et al. |
| 2007/0168038 A1 | 7/2007 | Trieu |
| 2007/0173939 A1 | 7/2007 | Kim |
| 2007/0179612 A1 | 8/2007 | Johnson et al. |
| 2007/0179615 A1 | 8/2007 | Heinz et al. |
| 2007/0179616 A1 | 8/2007 | Braddock, Jr. et al. |
| 2007/0179618 A1 | 8/2007 | Trieu et al. |

(56) References Cited

U.S. PATENT DOCUMENTS

| | | |
|---|---|---|
| 2007/0185578 A1 | 8/2007 | O'Neil et al. |
| 2007/0191953 A1 | 8/2007 | Trieu |
| 2007/0197935 A1 | 8/2007 | Reiley et al. |
| 2007/0198023 A1 | 8/2007 | Sand et al. |
| 2007/0198025 A1 | 8/2007 | Trieu et al. |
| 2007/0208426 A1 | 9/2007 | Trieu |
| 2007/0213717 A1 | 9/2007 | Trieu et al. |
| 2007/0219634 A1 | 9/2007 | Greenhalgh et al. |
| 2007/0233074 A1 | 10/2007 | Anderson et al. |
| 2007/0260255 A1 | 11/2007 | Haddock et al. |
| 2007/0270957 A1 | 11/2007 | Heinz |
| 2007/0282443 A1 | 12/2007 | Globerman et al. |
| 2008/0021557 A1 | 1/2008 | Trieu |
| 2008/0027437 A1 | 1/2008 | Johnson et al. |
| 2008/0027453 A1 | 1/2008 | Johnson et al. |
| 2008/0027454 A1 | 1/2008 | Johnson et al. |
| 2008/0051897 A1 | 2/2008 | Lopez et al. |
| 2008/0071356 A1 | 3/2008 | Greenhalgh et al. |
| 2008/0097611 A1 | 4/2008 | Mastrorio et al. |
| 2008/0125865 A1 | 5/2008 | Abdelgany |
| 2008/0140207 A1 | 6/2008 | Olmos et al. |
| 2008/0167657 A1 | 7/2008 | Greenhalgh |
| 2008/0177306 A1 | 7/2008 | Lamborne et al. |
| 2008/0195096 A1 | 8/2008 | Frei |
| 2008/0195210 A1 | 8/2008 | Mllijasevlo et al. |
| 2008/0221687 A1 | 9/2008 | Viker |
| 2008/0229597 A1 | 9/2008 | Malandain |
| 2008/0243251 A1 | 10/2008 | Stad et al. |
| 2008/0281346 A1 | 11/2008 | Greenhalgh et al. |
| 2008/0281364 A1 | 11/2008 | Chirico et al. |
| 2009/0018524 A1 | 1/2009 | Greenhalgh et al. |
| 2009/0030423 A1 | 1/2009 | Puno |
| 2009/0048678 A1 | 2/2009 | Saal et al. |
| 2009/0082872 A1 | 3/2009 | Beger |
| 2009/0105775 A1 | 4/2009 | Mitchell et al. |
| 2010/0082033 A1* | 4/2010 | Germain .......... A61B 17/1642 606/79 |
| 2010/0241177 A1 | 9/2010 | Schaller |
| 2010/0262242 A1 | 10/2010 | Chavette |
| 2010/0298832 A1 | 11/2010 | Lau |
| 2012/0239050 A1 | 9/2012 | Linderman et al. |
| 2012/0330314 A1* | 12/2012 | Schaller .......... A61B 17/1642 606/79 |
| 2013/0006232 A1* | 1/2013 | Pellegrino .......... A61B 17/3472 606/33 |

FOREIGN PATENT DOCUMENTS

| | | |
|---|---|---|
| DE | 202006005868 U1 | 6/2006 |
| EP | 0529275 A2 | 3/1993 |
| EP | 0 621 020 A1 | 10/1994 |
| EP | 1 157 676 | 11/2001 |
| EP | 1157676 A1 | 11/2001 |
| FR | 2586183 | 2/1987 |
| FR | 2712486 A1 | 5/1995 |
| FR | 2913331 | 12/2008 |
| WO | WO 93/04634 | 3/1993 |
| WO | WO 98/034552 | 8/1998 |
| WO | WO 00/67650 | 11/2000 |
| WO | WO 00/67651 | 11/2000 |
| WO | WO 01/10316 A1 | 2/2001 |
| WO | WO 02/17824 A2 | 3/2002 |
| WO | WO 02/30338 A1 | 4/2002 |
| WO | WO 02/43628 A1 | 6/2002 |
| WO | WO 02/47563 A1 | 6/2002 |
| WO | WO 02/071921 A2 | 9/2002 |
| WO | WO 03/007854 A1 | 1/2003 |
| WO | WO 03/020169 A2 | 3/2003 |
| WO | WO 03/022165 A1 | 3/2003 |
| WO | WO 03/028587 A2 | 4/2003 |
| WO | WO 03/059180 A2 | 7/2003 |
| WO | WO 03/101308 A1 | 12/2003 |
| WO | WO 2004/034924 | 4/2004 |
| WO | WO2004/034924 A2 | 4/2004 |
| WO | WO 2004/062505 A1 | 7/2004 |
| WO | WO 2004/082526 A2 | 9/2004 |
| WO | WO 2004/098420 A2 | 11/2004 |
| WO | WO 2004/108022 A1 | 12/2004 |
| WO | WO 2005/032433 A2 | 4/2005 |
| WO | WO 2006/047645 A2 | 5/2005 |
| WO | WO 2005/051246 A2 | 6/2005 |
| WO | WO 2005/081877 A2 | 9/2005 |
| WO | WO 2006/047587 | 5/2006 |
| WO | WO 2006/060420 A1 | 6/2006 |
| WO | WO 2006/066228 A2 | 6/2006 |
| WO | WO 2006/072941 | 7/2006 |
| WO | WO 2006/072941 A2 | 7/2006 |
| WO | WO 2007/022194 | 2/2007 |
| WO | WO2007/067726 A2 | 6/2007 |

OTHER PUBLICATIONS

Edeland, H.G., "Some Additional Suggestions for an Intervetebral Disc Prosthesis", Journal of BioMedical Engr., vol. 7(1), pp. 57-62, Jan. 1985.

U.S. Appl. No. 60/557,246, filed Mar. 29, 2004, entitled: Device and Methods to Reduce and Stabilize Broken Bones.

U.S. Appl. No. 60/689,570, filed Jun. 13, 2005, Inventor Tzony Siegal, entitled: Directional Drilling System.

John A. Carrino, Roxanne Chan and Alexander R. Vaccaro, "Vertebral Augmentation: Vertebroplasty and Kyphoplasty", Seminars in Roentgenology, vol. 39, No. 1 Jan. 2004, pp. 68-84.

Ajeya P., Joshi, M.D., and Paul A. Glazer, M.D., "Vertebroplasty: Current Concepts and Outlook", 2003, 9 pages, From: http://www.spineuniverse.com/displayarticle.php/article2076.html.

* cited by examiner

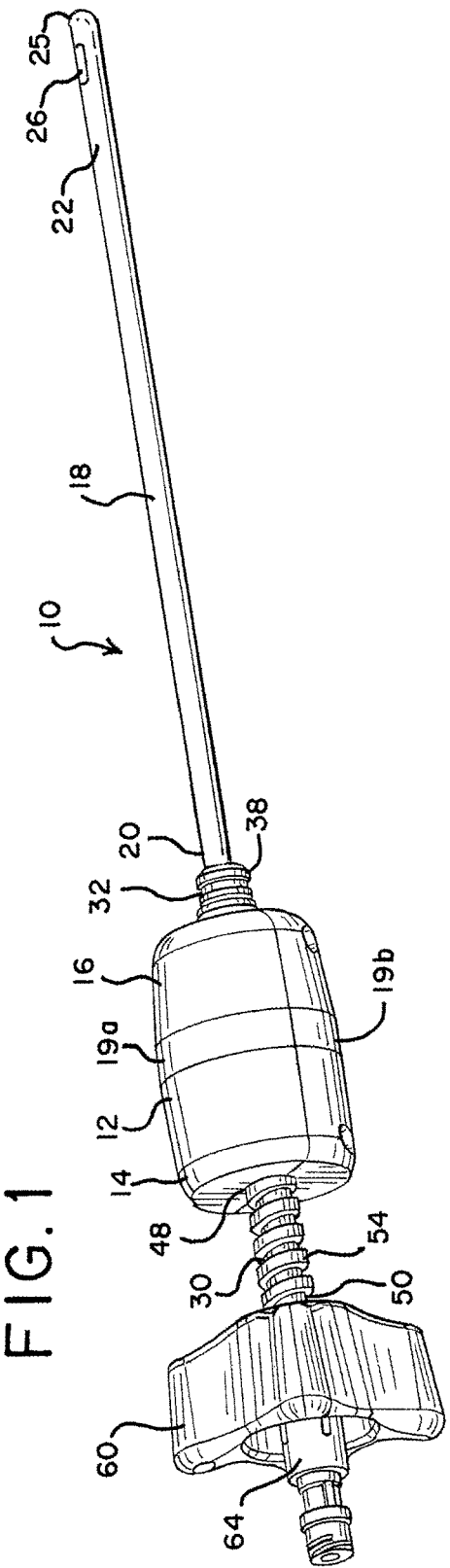

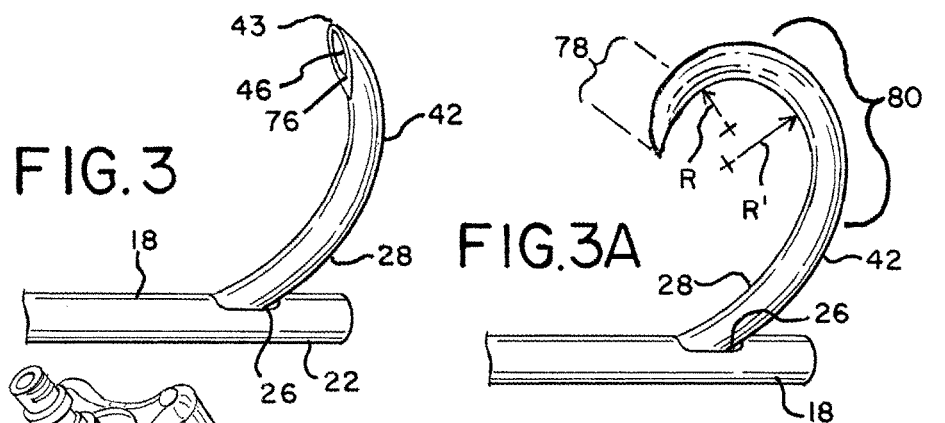
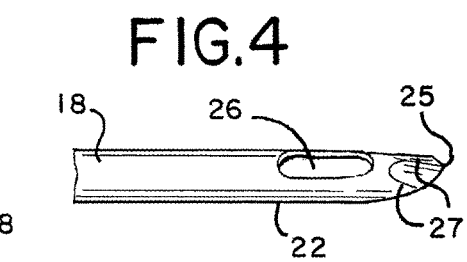
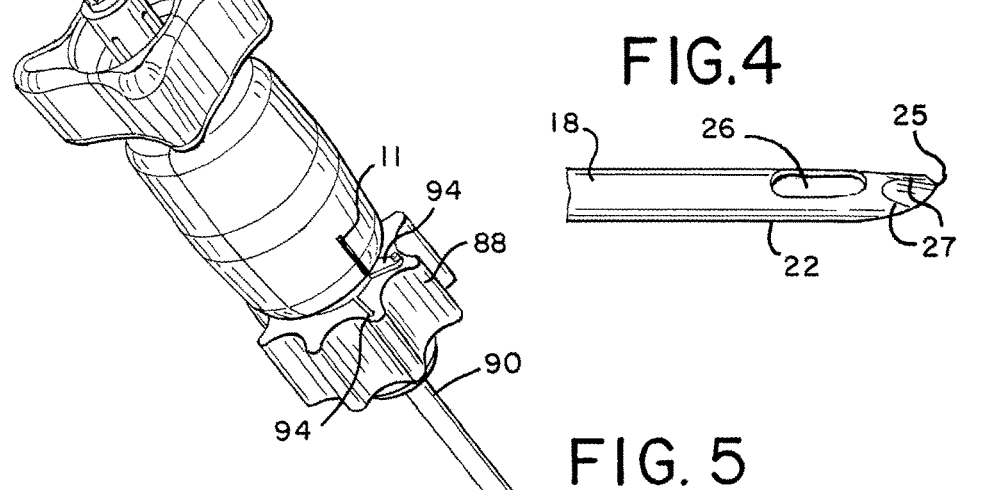
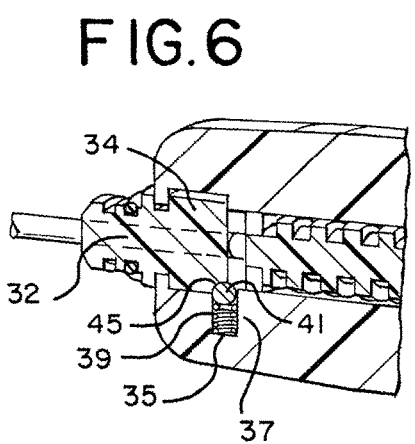
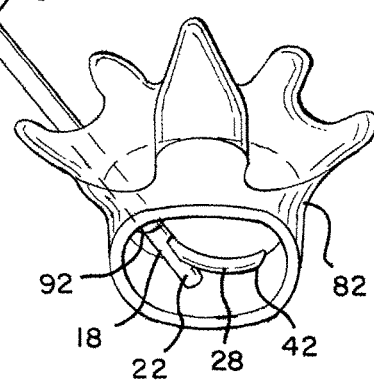

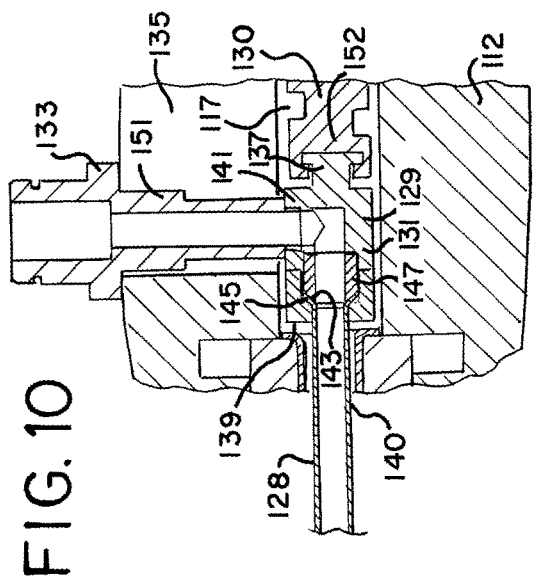
FIG. 7
FIG. 8
FIG. 10
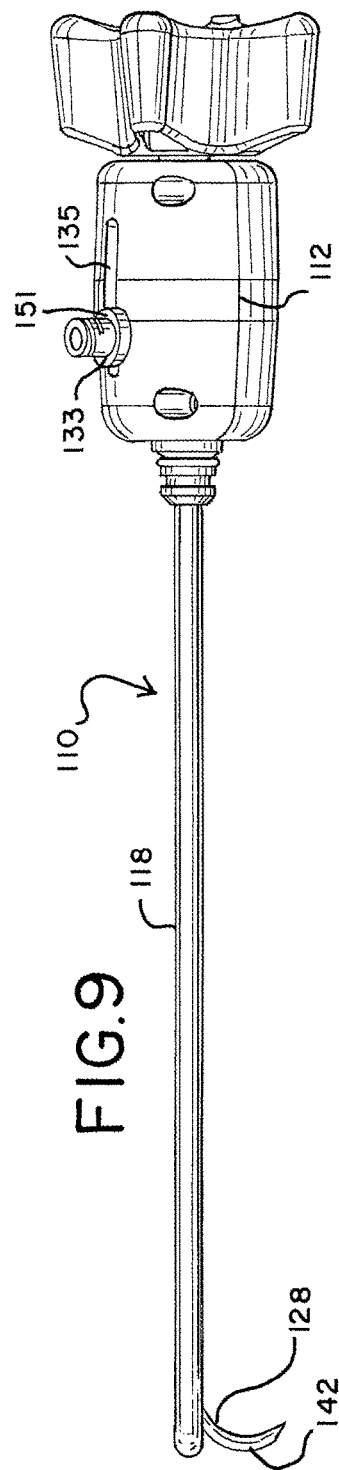
FIG. 9

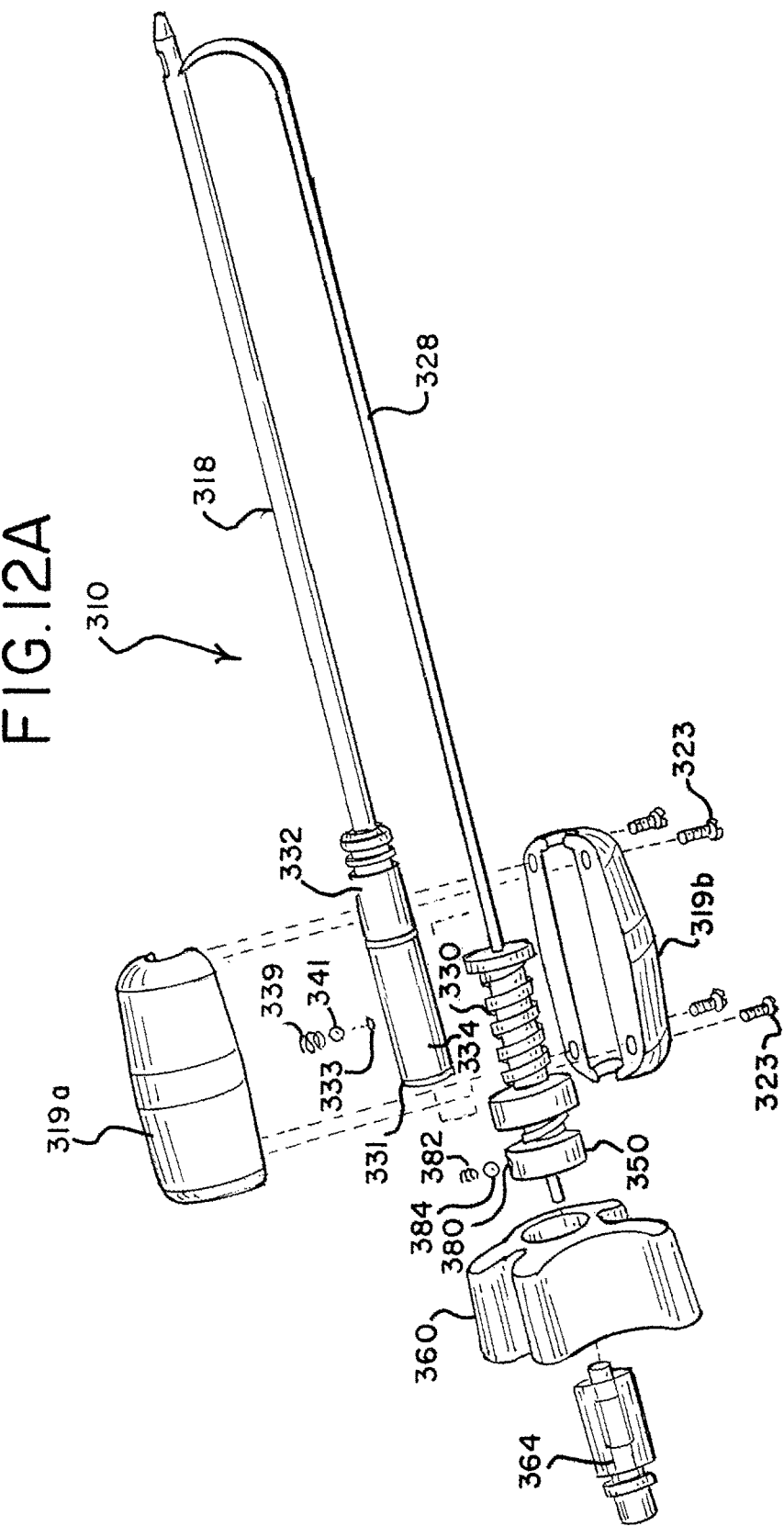

DEVICES AND METHODS FOR TREATING BONE TISSUE

TECHNICAL FIELD

The present disclosure generally relates to devices and methods employed in minimally invasive surgical procedures. More particularly, the present disclosure generally relates to various devices and methods for injecting material into and/or forming channels in a treatment site within a patient, especially into bone including vertebral bone tissue for the treatment of vertebral compression fractures.

BACKGROUND

It is often necessary or desirable to administer, deliver or inject material into a particular target location or zone in the human body for therapeutic or diagnostic treatments or procedures. The injectable material can include a variety of different fluids, including orthopedic cements, bone and other bone augmentation materials, drugs, contrast agents, cell-based treatment materials such as stem cells, and other fluids for a variety of different diagnostic or therapeutic treatments or procedures. Although the subject matter of this disclosure is not limited to orthopedic treatments in general or spinal treatments in particular, treatment of spinal conditions, including treatment of vertebral compression fractures, is an area where injection of a material into the vertebral body is a particularly common treatment.

A vertebral compression fracture (VCF) is a common spinal condition that typically involves the injection of material as part of the treatment. A vertebral compression fracture is a crushing or collapsing injury to one or more vertebrae. Vertebral compression fractures are generally, but not exclusively, associated with osteoporosis, metastasis, and/or trauma. Osteoporosis reduces bone density, thereby weakening bones and predisposing them to fracture. The osteoporosis-weakened vertebrae can collapse during normal activity and are also more vulnerable to injury from shock or other forces acting on the spine. In severe cases of osteoporosis, actions as simple as bending forward can be enough to cause a vertebral compression fracture.

One technique used to treat vertebral compression fractures is injection of a bone augmentation material directly into the fractured vertebral body. This procedure is commonly referred to as vertebroplasty. More particularly, vertebroplasty involves injecting bone augmentation material (for example, bone cement, bone growth agent, allograph material or autograph material) into the collapsed vertebra to stabilize and strengthen the crushed vertebra. Other techniques for treating vertebral compression fractures employ the injection of bone cement into cavities formed within the cancellous bone of a vertebral body. Such cavities may be formed by removal of cancellous bone using cavity/channel creation tools or by compaction of the cancellous bone using expansion of balloons within the vertebral body. Bone cement is also injected in or around implants that are inserted into the vertebral body to separate and support the vertebral endplates.

Injection of bone augmentation material into the vertebral body, however, sometimes carries with it the risk of "extravasation." For example, in vertebroplasty and certain other procedures, bone augmentation material, and particularly bone cement, is introduced directly into the vertebral body with the physician preferably viewing the cement dispersion via fluoroscopy during the procedure. This type of injection requires particular care as there is a risk of extravasation, which includes undesired leakage or dispersion of the bone augmentation material into undesired areas, such as into the vicinity of the spinal cord or nerves.

Accordingly, although the subject matter described herein is not limited to orthopedic or spinal treatments, it has particular benefits in the treatment of VCF, and is significant because there has been and continues to be a long felt need for devices and methods to control or limit the flow materials during injection into the body and in particular to control and/or limit the flow of bone augmentation material, such as bone cement and related fluids, injected into the vertebral body during vertebroplasty and certain other related VCF treatments.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a device for injecting material into a body includes a housing having proximal and distal end portions. The device also includes a deployment cannula having a proximal end portion, a distal end portion and a lumen that extends from an opening in the proximal end portion of the deployment cannula to an opening in the distal end portion of the deployment cannula. The proximal end portion of the deployment cannula is operatively connected to the distal end portion of the housing. The distal end portion of the deployment cannula is configured for insertion into the body. The device also includes a rotary drive member having a proximal end portion and a distal end portion. The rotary drive member extends through a proximal end opening in the housing wherein rotational movement of the drive member relative to the housing results in distal linear movement of the drive member. The device further includes an elongated injection member for injecting material into the body. The elongated injection member is disposed and moveable within the lumen of the deployment cannula. The elongated injection member has a proximal end portion, a distal end portion and a lumen that extends between an opening in the proximal end portion of the elongated injection member and an opening in the distal end portion of the elongated injection member. The proximal end portion of the elongated injection member is operatively connected to the rotary drive member such that distal linear movement of the drive member advances the elongated injection member distally through the lumen of deployment cannula to extend the distal end portion of the elongated injection member out of the distal end portion opening of the deployment cannula.

In another aspect, the devices of the present disclosure may include a torque limiting member such that the deployment cannula rotates, with certain torque limits, as the housing is rotated. The torque limiting member discontinues transmission of force or releases when a threshold level of torque is encountered.

In another aspect, the devices of the present disclosure may include a force or drive limiting member such that the elongated injection member advances or is driven with certain force limits, as the elongated member penetrates the bone. The force limiting member discontinues drive force to the elongated member or releases when a threshold level of force is encountered.

In yet another aspect, the elongated injection member of the devices of the present disclosure may include a distal end portion that has a Tuohy-Huber tip.

In another aspect, the elongated injection member of the devices of the present disclosure may include a distal end portion having a plurality of differing radii of curvature. The distal end portion having differing radii of curvature may also have a Tuohy-Huber tip.

In a further aspect, a medical needle includes an elongated tubular shaft that has a proximal end portion, a distal end portion and a lumen that extends from an opening in the proximal end portion to an opening in the distal end portion. At least the distal end portion of the elongated shaft has an unconstrained arcuate configuration defined by differing radii of curvature along a curve of the distal end portion of the elongated shaft. The opening in the distal end portion is defined by a flat surface located at a distal tip of the elongated shaft. At least the distal end portion of the cannula being movable between a constrained substantially linear configuration that is constrained by an external constraining force and the arcuate unconstrained configuration, when the external straining force is released.

BRIEF DESCRIPTION OF THE DRAWINGS

In the course of this description, reference will be made to the accompanying drawings, wherein:

FIG. 1 is a perspective view of one embodiment of a material delivery device of the present disclosure;

FIG. 2 is a cross-sectional view of the material delivery device of FIG. 1 with an internal injection member in an advanced position extending from a side opening in a deployment cannula;

FIG. 3 is a perspective view of the distal end portion of the material delivery device of FIG. 1 showing an alternative configuration of the distal end portion of the internal elongated injection member extending from a side opening in the distal end portion of the deployment cannula;

FIG. 3A is a side view of the distal end portion of the material delivery device of FIG. 1 showing an alternative configuration of the distal end portion of the elongated injection member extending from a side opening in the distal end portion of the deployment cannula;

FIG. 4 is a perspective view of an alternative configuration of the distal end portion of the deployment cannula of the material delivery device;

FIG. 5 is a perspective view of the material delivery device being inserted through an access cannula and into a vertebral body;

FIG. 6 is a partial enlarged cross-sectional view of one configuration of a torque limiting device that may be employed in the material delivery device of FIG. 1;

FIGS. 7 and 8 are cross-sectional views illustrating the operation of the torque limiting device of FIG. 6;

FIG. 9 is a perspective view of another embodiment of a material delivery device in accordance with the present disclosure;

FIG. 10 is an enlarged cross-sectional view of one configuration of a connector for connecting an injectable material supply to an elongated injection member of the device of FIG. 9;

FIG. 12A is an exploded view of another embodiment of a material delivery device in accordance with the present disclosure.

Corresponding reference numerals indicate corresponding parts throughout the several views.

DETAILED DESCRIPTION

Although detailed embodiments of the present subject matter are disclosed herein, it is to be understood that the disclosed embodiments are merely exemplary, and the subject matter may be embodied in various forms. Therefore, specific details disclosed herein are not to be interpreted as limiting the subject matter claimed, but merely as examples to illustrate and describe the subject matter and various aspects thereof.

Disclosed herein are devices and methods for forming channels and/or injecting material into a treatment site within a patient. Such treatment sites may include bones and bone tissue. The devices may be particularly useful in treating injured or damaged vertebral bodies, such as those having compression fractures. While the devices are described herein in relation to vertebral bodies, the devices are not limited to such and may be used to treat other tissues and parts of the body as well.

Figure 2A:
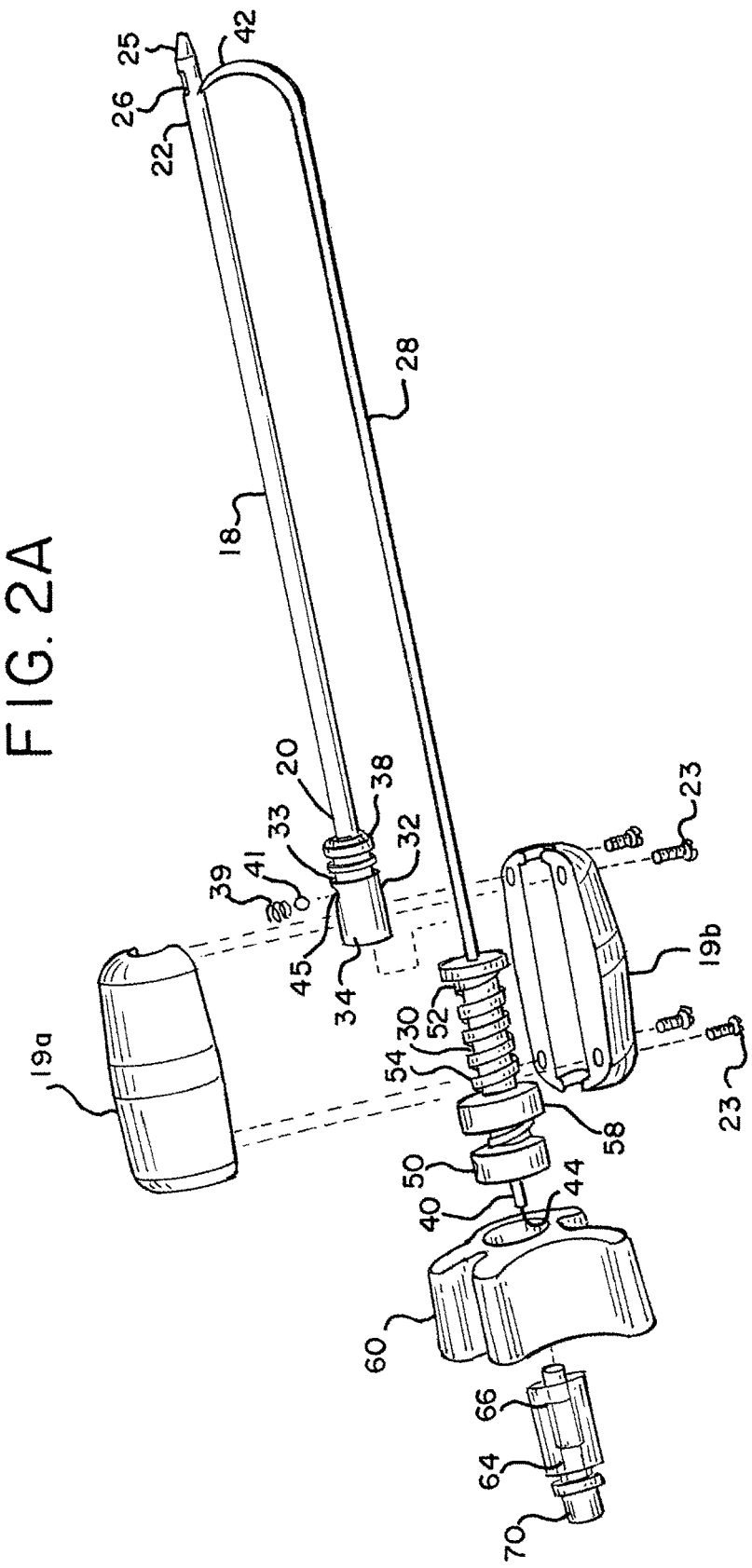
FIG. 2A is an exploded view of the material delivery device of FIG. 1.

FIGS. 1, 2 and 2A illustrate one embodiment of a material injection device 10 in accordance with the present disclosure. Injection device 10 includes, among other features, a housing 12, a deployment cannula 18, an elongated injection member 28, which also may serve as a channel forming member or bone tamp, (FIG. 2) and a drive member 30, such as a rotary or threaded drive member. As explained in more detail below, the elongated injection member 28 is moveable within deployment cannula 18 and through a distal opening, such as side opening 26, of the deployment cannula 18 wherein the elongated injection 28 may be employed to form a channel(s) through the tissue of the treatment site and/or inject material into a treatment site. The channel(s) may be formed prior to the injection of material or substantially simultaneously with the injection of material. Alternatively, multiple channels may first be formed prior to injection of material and then material may be injected into the multiple channels.

The housing 12 has a proximal end portion 14, a distal end portion 16 and an inner cavity 17 (FIG. 2). Referring to FIGS. 1 and 2A, the housing 12 may include first and second halves or shells 19a/19b which are attached to each other in any suitable manner, such as with screws, adhesive or ultrasonic welding, to form housing 12. As illustrated in FIG. 2A and later in FIGS. 7a and 8, housing halves 19a/19b are shown attached to each other by screws 23.

Deployment cannula 18 is preferably connected to and extends from the distal end portion 16 of housing 12. Deployment cannula 18 includes a proximal end portion 20, a distal end portion 22 and a lumen 21 extending from an opening 24 (FIG. 2) in the proximal end portion 20 to an opening, such as side opening 26, in the distal end portion 22. In the illustrated embodiment, opening 26 in the distal end portion of deployment cannula 18 is a side opening located in a sidewall of the deployment cannula 18. In other embodiments, opening 26 may be located at the distal tip 25 of the deployment cannula 18. Additionally, as better seen in FIG. 4, the distal tip 25 of the deployment cannula 18 may include a sharp point or edges for passing or cutting through tissue as the distal end portion 22 of the deployment cannula 18 is inserted through tissue and into the treatment site. In some applications, instead of using a separate introduction trocar or cannula, the distal tip 25 itself may act as an access stylet or may be used as the access tool that is initially inserted through layers of outer tissue and into the treatment site. In the embodiment illustrated in FIG. 4, the distal tip 25 of the deployment cannula 18 is a multifaceted member that includes edges 27 for cutting through tissue or penetrate through bone.

Turning back to FIGS. 1, 2 and 2A, the proximal end portion 20 of deployment cannula 18 may be connected to housing 12 by a hub 32. In the illustrated embodiment, hub 32 includes a proximal end portion 34 positioned within an opening 36 in the distal end portion 16 of housing 12 and a distal end portion 38 extending from opening 36. The proximal end portion 20 of deployment cannula 18 is connected to hub 32, for example by adhesive or weld based on the material used, and extends through an inner passageway of hub 32 into cavity 17 of housing 12. Deployment cannula 18 and housing 12 may be rotatable or non-rotatable relative to each other. In the illustrated embodiment, deployment cannula 18 and housing 12 are rotatable relative to each other about longitudinal axis A (FIG. 2). In this embodiment, deployment cannula 18 is fixedly connected to hub 32 wherein hub 32 is rotatably mounted to housing 12. A portion 15 of housing 12 adjacent opening 36 projects into a mating channel 33 circumferentially extending around hub 32. The mating between portion 15 of housing 12 and channel 33 of hub 32 connects hub 32 to housing 12 in a fixed axial position while allowing housing 12 to rotate about axis A relative to hub 32. In another configuration, deployment cannula 18 may be rotatably connected to hub 32 which is fixedly connected to housing 12. And in another embodiment, deployment cannula 18 is fixed to hub 32 and hub 32 is fixed to housing 12.

In other configurations, the delivery cannula 18 is connected to the housing 12 such that the delivery cannula 18 rotates about axis A (FIG. 2), within certain torque limits, as housing 12 is rotated thereabout. In such embodiments, the device 10 may include a torque limiting mechanism, such as a torque break-away or clutch, that transmits rotational force from the housing 12 to the delivery cannula 18 until a threshold of rotational resistance is encountered by the delivery cannula 18. At such time, the torque limiting mechanism will release and discontinue transmission of rotational forces from the housing 12 to the delivery cannula 18 and the delivery cannula 18 with remain stationary relative to the patient or surgical site as the housing continues to rotate about axis A. The torque limiting mechanisms reduces the risk of damage to the device and/or trauma to the patient that may occur when undue rotational resistance is encountered in the treatment site. For example and as explained in more detail below, after the distal end portion 22 of delivery cannula 18 is placed within a treatment site, the housing 12 may be rotated to locate the distal end portion 22 of the delivery cannula 18 (e.g., the side opening 26) into a preferred or different position within the treatment site. If the delivery cannula 18 encounters a threshold level of rotational resistance, the torque limiting mechanism will discontinue transmission of torque from the housing 12 to the delivery cannula 18 which will result in the cannula remaining stationary within the treatment site while the housing is allowed to continue to rotate. The torque limiting feature may also prevent damage to the injection device, such as in a situation wherein the injection member 28 has been deployed therefrom. In such applications, undue force during rotation of device 10 into a preferred or different position may develop between the elongated injection member 28 extending from distal opening 26 of the deployment cannula 18 and adjacent bone, for example, and may result in damage to the elongated injection member 28 that could make it difficult to inject and/or retract the elongated injection member 28 back into the deployment cannula 18 and out of the treatment site. With the torque limiter, when the resistance to torque reaches a certain threshold, the torque limiting mechanism releases and discontinues the transmission of torque from the housing 12 to the deployment cannula 18 therefor preventing damage to the device and/or surrounding bone or tissue.

The torque limiting mechanism may be any suitable mechanism for limiting or discontinuing the transmission of torque, such as a shear pin, friction fit, magnetic forces, or ball and detent. The design of the mechanism is meant to limit the peak torque and thus the peak force applied to the elongated injection member 28 in all configurations of deployment such that it remains intact. FIGS. 6-8 illustrate one embodiment of a ball and detent torque limiting mechanism that may be used with any of the devices disclosed herein. The torque limiting mechanism includes a detent surface (such as a notch or recess) located in either the hub 32 or the housing 12 wherein a ball is biased into the detent. The mating between the ball and the detent normally transmits the rotational force from the housing 12 to the hub 32 to rotate the delivery cannula 18 with the housing 12. In the embodiment illustrated in FIGS. 6-8, the proximal portion 34 of hub 32 includes a detent 45 in a sidewall thereof. Housing 12 includes a channel 35 located in an inner wall 37 of the housing 12 wherein a biasing member 39, such as a coiled spring, biases a ball 41 into detent 45. The engagement of ball 41 and detent 45 transmits rotational force from housing 12 to hub 32. When the deployment cannula 18 encounters a certain threshold of rotational resistance that exceeds the biasing force holding the ball 41 in the detent 45, the ball slips out of the detent 45, and the housing 12 is allowed to continue to rotate relative to the hub 32. Thus, the deployment cannula 18 remains stationary within the treatment site as the housing continues to rotate.

Referring back to FIG. 2, elongated injection member 28 is preferably an elongated, hollow tube or shaft, which is at least partially disposed in and movable through the lumen 21 of deployment cannula 18. Elongated injection member 28 includes a proximal end portion 40, a distal end portion 42 and an internal material flow lumen extending from an opening 44 in the proximal end portion 40 to an opening 46 in the distal end portion 42.

Rotary drive member 30, such as a threaded drive screw, is positioned within an opening 48 (which is in communication of cavity 17) in the proximal end portion 14 of housing 12. The threaded drive member 30 includes a proximal end portion 50, a distal end portion 52 and threads 54 that at least partially extend along the length of threaded drive member 30. Housing 12 includes corresponding threads 56, which may be integral with the housing 12 or may be a separate component attached (glued, welded or press-fitted) to housing 12. In the illustrated embodiment, corresponding threads 56 are formed by a nut 58 that is affixed to the housing 12 at or adjacent to the opening 48 in the proximal end portion 14 of the housing 12. When threaded drive member 30 is rotated in one direction, threaded drive member 30 travels, or is otherwise advanced linearly, in a distal direction into the cavity 17 of housing 12. When threaded drive member 30 is rotated in the other direction, threaded drive member 30 travels, or is retracted linearly, in a proximal direction outwardly of opening 48 of housing 12. Threaded drive member 30 may include a gripping member 60, such as a handle or knob, preferably located at the proximal end 50 of the thread drive member 30 such that a user may grip gripping member 60 to more easily rotate the threaded drive member 30.

The proximal end portion 40 of elongated injection member 28 is operably connected to threaded drive member 30. In the illustrated embodiment, the proximal end portion 40 of elongated injection member 28 extends proximally from the proximal end opening 24 of deployment cannula 18 and is connected to rotary drive member 30. More specifically, the proximal end portion 40 of the elongated injection member 28 is rotatably connected to drive member 30 such that when drive member 30 is rotated relative to housing 12 to advance or retract the threaded drive member 30, elongated injection member 28 does not rotate therewith. Elongated injection member 28 does, however, travel linearly in the proximal and distal directions with the drive member 30. Thus, when the drive member 30 is rotated in one direction, the elongated injection member 28 travels or is advanced linearly in the proximal direction relative to housing 12 and deployment cannula 18. When the drive member 30 is rotated in the other direction, the elongated injection member 28 travels or is retracted linearly in the proximal direction.

Comparing FIGS. 1 and 2, as rotary drive member 30 is rotated so as to distally advance the drive member 30 into inner cavity 17 of the housing 12, the drive member 30 distally advances the elongated injection member 28 through the lumen 21 of deployment cannula 18 and out of distal opening 26 of the deployment cannula 18. The pitch size of threads 54 of the illustrated drive member 30 directly affects or determines the distance or amount of linear travel (i.e., distal advancement and proximal retraction) of the drive member 30 and elongated injection member 28 connected thereto that takes place upon each increment of rotation of the drive member 30. As such, rotation of the drive member 30 provides for controlled, selected incremental, continuous, and/or fine advancement of the elongated injection member 28 out of the distal end opening 26 of the deployment cannula 18 and into the treatment site. As a result, the operator of device 10 may selectively advance and retract the distal end portion 42 of the elongated injection member 28 into and from the treatment site. The pitch size of the threads 54 may vary along the length of the threaded drive member 30 or may vary between devices, depending on the desired application.

In the embodiment illustrated in FIG. 2, the proximal end portion 40 of the elongated injection member 28 preferably extends through drive member 30 and includes a portion 62 that extends proximally past the proximal end portion 50 of drive member 30. Portion 62 of elongated injection member 28 is operably connected to an injectable material-receiving port 64. Port 64 includes a distal end portion 66 having a distal end opening 68, which opening 68 may be operatively connected to and receive portion 62 of the elongated injection member 28 so that proximal end opening 44 of the elongated injection member 28 is in fluid communication with passageway 74 of port 64. Port 64 also includes a proximal end 70 having a proximal end opening 72 wherein passageway 74 extends from proximal opening 72 to distal end opening 68. Proximal end 70 is configured to be connected to a supply of injectable material. In one embodiment, proximal end portion 70 defines or includes a luer-type connector. The injectable material includes but is not limited to, bone filler, bone augmentation material, bone cement, autograph, allograph, osteoconductive materials, therapeutic materials, genetic materials, cells, contrast agents, and/or drugs. The material supply may be, any suitable source for injecting material under pressure, such as, for example, a syringe containing material, such as the screw type syringe 111 shown in FIG. 11. Such material may be injected from the supply of injectable material through the port 64 and into the lumen of the elongated injection member 28. The material travels through the lumen of the elongated injection member 28 and exits through the opening 46 in the distal end portion 42 of the elongated injection member 28 into the treatment site.

In one alternative, the material-receiving injection port 64 is a rotatable luer connector wherein proximal end portion 70 and distal end portion 66 rotate relative to one another. This allows the device 10 to be rotated without the need for rotating the supply of injectable material.

Referring to FIGS. 2-3A, at least the distal end portion 42 of the elongated injection member 28 has a generally arcuate configuration when extending from distal opening 26 of the deployment cannula 18. In one embodiment, the distal end portion 42 of the elongated injection member 28 has an initial generally arcuate unconstrained configuration which is moveable i.e., deformable, into a substantially straight constrained configuration when an external constraint is placed on the distal end portion 42 of the elongated injection member 28. "Substantially straight" includes some variation or undulation and is not limited to completely straight. The distal end portion 42 of elongated injection member 28 is then moveable back to the generally arcuate unconstrained configuration when the constraint is removed. For instance, at least the distal end portion 42 of the elongated injection member 28 has an initial unconstrained arcuate configuration, such as the configurations illustrated in FIGS. 2-3A and 13. The distal end portion 42 of the elongated injection member 28 is inserted into the lumen 21 of deployment cannula 18 which deployment cannula 18 constrains the distal end portion 42 into a substantially straight or linear configuration for passage through the lumen 21 of the deployment cannula 18. Upon exiting out of the distal end opening 26 of the deployment cannula 28, the cannula constraint is removed and the distal end portion 42 of the elongated injection member 28 returns to its initial or similar arcuate configuration. In other words, at least the distal end portion 42 of the elongated injection member 28 is moveable or changeable from a substantially straight or linear configuration for passage through the deployment cannula 18 to a non-straight configuration, such as the curved or arcuate configurations illustrated in FIGS. 2-3A, upon exiting distal end opening 26 of the deployment cannula 18.

Movement of the elongated injection member 28 between the substantially straight configuration and the generally arcuate configuration may be achieved in any variety of ways, including but not limited to use of shape memory materials, a plurality of layers of material, varying thickness of the material, incorporation of a tensioning member, slotting, cutting, or pre-setting the shape of the material or any combination of the above. Additionally, the length or extent of curvature of the distal end portion 42 of the elongated injection 28 member may be different depending on the desired application. For example, the distal end portion may have only a small amount of curvature or extend to a full circle or coil or to a plurality of helical or spiral coils. More specifically, the arcuate or curved distal end portion 42 may extend to form a generally arc-shaped portion (e.g., a generally 45°, 90° or 180° or 270° or up to 360° arc), or may extend in a circular-shape or spiral-shape substantially lying in a single plane or extending in a helical shape, with a vertical extent extending through several different planes. As used herein, the term "spiral" refers to a coil-shaped structure that lies within a single plane, while the term "helical" refers to a coil-shaped structure that has a three-dimensional component or does not lie in one plane.

FIGS. 3 and 3A illustrate exemplary configurations of the distal end portion 42 of elongated injection member 28 that have reduced or anti-coring features, which features may be used alone or in combination in any of the injection devices disclosed herein. It is known that when the distal end portion of a needle or hollow tube or shaft is inserted into tissue, there may be a tendency for the distal opening to core tissue. Such coring may not be desirable in certain applications and the cored tissue may undesirably clog the lumen of the needle, tube or shaft. In one example of the present subject matter, referring first to FIG. 3, the distal end portion 42 of the elongated injection member 28 preferably resists coring, and extends from opening 26 of the deployment cannula 18 in a generally arcuate configuration. The distal tip 43 of the elongated injection member 28 includes an opening 46 which opens in a generally radial direction inwardly of the curved configuration of the distal end portion 42 of elongated injection member 28. In the illustrated embodiment elongated injection member 28 includes a Tuohy-Huber type tip and opening. Such Tuohy-Huber type tips are shown and described in U.S. Pat. No. 2,409,979 to Huber, hereby incorporated by reference. Generally, distal tip 43 is a curved tip that includes a flat beveled or inclined surface 76 that defines the opening 46, which opening 46 opens in a generally radial direction inwardly of the curved configuration of the distal end portion 42 of elongated injection member 28. The surface 76 is substantially flat and lies at an angle relative to the axis of tubular elongated injection member 28. The distal tip 43 may, but does not necessarily, come to a sharp point for piercing tissue. As mentioned above, one of the advantages of employing the Tuohy-Huber type tip is that is tends to reduce coring of tissue during insertion of the elongated injection member 28 into treatment site for forming channels and/or injecting materials. Specifically, as the distal end portion 42 of the elongated injection element 28 exits opening 26 of the deployment cannula 18 and curves, the opening 46 in the Tuohy-Huber type tip 43 faces radially inwardly which acts to somewhat shield the opening 46 and assists in preventing the opening 46 from coring tissue.

Turning now to FIG. 3A, the distal end portion 42 of the elongated injection member 28 may include sections having different radii of curvature. For example, a more distal section 78 of the distal end portion 42 may have a tighter or smaller radius of curvature R than a more immediately adjacent proximal section 80 of the distal end portion 42. In the illustrated embodiment, section 78 of the distal end portion 42 of elongated injection member 28 may have a radius of curvature R which is smaller than the radius of curvature R' of the proximally adjacent section 80. The smaller or tighter radius of curvature of section 78 directs opening 46 more inwardly relative to the curvature of the distal end portion 42 of the elongated injection member 28, which further assists in preventing coring of tissue as the elongated injection member 28 is inserted into the treatment site. In another embodiment, an obturator can be inserted inside elongated injecting member 28 to close opening 46 while it is inserted into the treatment site for injecting material and/or creating channels. The obturator may be retrieve prior to bone cement injection (not shown). When the distal end portion 42 is formed from the shape memory material Nitinol, the varying radii of the distal end portion 42 can be formed during the shape setting process. The shape setting process may include the use of progressive shape setting cycles with dies having progressively tighter (smaller) radius features. In another embodiment, the shape setting may include a single die or die like feature setting the shape of the distal end portion 42.

In one embodiment, the distal end portion 42 of the elongated injection member 28 includes both a Tuohy-Huber type tip and a distal section of distal end portion 42 has a tighter or smaller radius of curvature than an immediate adjacent proximal section of the distal end portion 42. The combination of the Tuohy-Huber tip and the tighter radius of curvature of the distal section orientates the distal opening 46 of the elongated injection member 28 inwardly to assist in the prevention of coring material as the elongated injection member 28 is inserted into the treatment site.

The elongated injection member may be made of different materials. For example, when the distal end portion 42 of the elongated injection member 28 is made from a shape memory material, such as Nitinol, the proximal end portion 40 of elongated injection member 28 may be made of a different material, such as stainless steel. A distal end portion 42 made of a shape memory metal may be joined to a proximal end portion 40 of the same or other material by any suitable manner, such as by soldering or brazing. In another alternative structure, a Nitinol tube defining the distal end portion 42 may be press fitted to a stainless steel tube defining the proximal end portion 40. Such a press fitting processes may take place in low temperatures so as to cool the Nitinol material to its martensitic phase. In one embodiment, dry ice or a low temperature compressed gas can be used to cool the Nitinol tube. While in the martensitic phase the material is more malleable and can be easily press fitted to the stainless steel tube. When the Nitinol temperature returns to room temperature, the Nitinol returns to its superelastic phase, creating a strong radial lap joint. In another process, the stainless steel to may be swaged and thus yielded while the Nitinol remains in the super elastic phase. Swaging creates a strong radial lap joint between the two tubes.

FIG. 5 shows the deployment cannula 18 of device 10 being inserted into a vertebral body 82 through an access member, such as access cannula 84. The access cannula 84 includes a proximal end portion 90, a distal end portion 92 and a lumen extending therethrough. A handle 88 is located at the proximal end portion 90 of access cannula 84. The distal end portion 92 of the access cannula 84 is introduced into a treatment site for gaining access to the treatment site. The distal end portion 92 of access cannula 84 can be introduced into a treatment site by any suitable methods which may include the use of Jamshidi needles, stylets, trocars, dilators and the like.

The access cannula 84 or handle 88 may include indicators or markings thereon to indicate to the operator the orientation of the tools inserted therethrough or to align the tools in a desired orientation within the treatment site. Such indicators may include visual marks 94 on the handle 88 or marks on the access cannula 84. Device 10 may also include indicators or markers that indicate the orientation of the device 10 within the treatment site. For example, the device 10 may include visual indicators 11 indicating the location of opening 26 and/or the trajectory of the elongated injection member 28 as it exits the distal opening 26 of the deployment cannula 18. During the treatment of vertebral bodies, such alignment may be useful wherein a channel creating device has been inserted through the access cannula 84 and into the interior region of the vertebral body to form channels within the cancellous bone of the vertebral body prior to insertion of device 10. After the channel creation device has been withdrawn from the access cannula 84, device 10 is inserted therethrough and the indicators 11 on the device 10 and indicators 94 on handle 88 may be aligned to orient device 10 and the distal end portion 42 of elongated injection member 28 in a desired orientation relative to the channels created by the channel creation device. In another embodiment, device 10 is used to first create channels and then the channels are re-cannulated later to deliver the injectable materials created previously by device 10. In another embodiment device 10 may be used as a standalone device to create a channel and then inject bone cement into the channel before a second or multiple channels are created.

Figure 11:
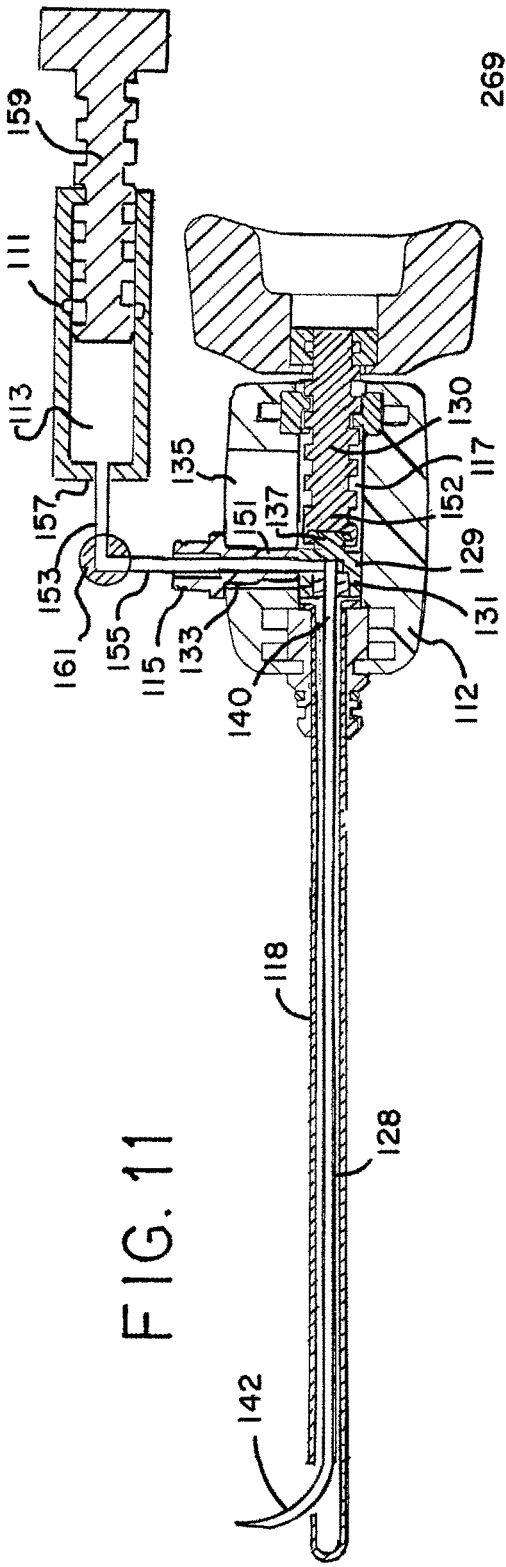
FIG. 11 is a cross sectional view of the material delivery device of FIG. 9.

FIGS. 9-11 illustrate another embodiment of an injection device 110 of the present disclosure. The injection device 110 is similar to injection device 10 in several aspects, including having a housing 112, a deployment cannula 118 and an elongated injection member 128. Referring to FIG. 11, the proximal end portion 140 of elongated injection member 128 may be operatively connected to the supply of injectable material 113 through an L-shaped connector 129. The L-shaped connector 129 includes a first portion 131 that is located within cavity 117 defined by housing 112 and a second portion 133 extending out of housing 112 through a slot 135 in the wall of housing 112. The first portion 131 of L-shaped connector is operably connected to the proximal end portion 140 of the elongated injection member 128. The second portion 133 of the L-shaped connector 129 extending through slot 135 of the housing 112 is operably connectable to a supply of injectable material 113 such as syringe. The second portion 133 of the L-shaped connector may include for example, a luer-type connector at a terminal end 115 thereof. A proximal portion or surface 137 of the L-shaped connector 129 is engaged by the distal end portion 152 of the rotary drive member 130 such that the L-shaped connector 129 and the elongated injection member 128 connected thereto moves proximally and distally with the rotary drive member 130.

FIG. 10 illustrates one embodiment of the L-shaped connector 129, the L-shaped connector 129 may include a first compression sleeve 139 on the leg of the L that is attached to the proximal end portion 140 of the elongated injection member 128 and a second compression sleeve 141 that is on the upright portion of the L connector and is attached to an injectable material receiving port 151. The first compression sleeve 139 and the second compression sleeve 141 may be attached to one another by a threaded connection, press fit or weld. The proximal end portion 140 of the elongated injection member 128 may include a radially extending flange portion 143 that abuts a tapered inner wall 145 of the first compression sleeve 139. Furthermore, the L-shaped connector 129 may include a retaining member, such as a crush washer 147, located in the first compression sleeve 139. The crush washer 147 forces the flange portion 143 of the elongated injection member 128 against inner tapered wall 145 to create a seal therewith. The crush washer 147 may apply a sufficient force to form a seal therebetween but still allow the elongated injection member 128 to rotate relative to the L-shaped connector 129.

As shown in FIGS. 10 and 11, the proximal portion 137 of the L-shaped connector 129 is rotatably connected to the distal end portion 152 of the rotary drive member 130 such that the rotary drive member 130 may rotate relative to the L-shaped connector 129, but the L-shaped connector 129 travels linearly in the proximal and distal direction with the rotary drive member 130 in cavity 117 of housing 112. As the L-shaped connector 129 moves proximally and distally within cavity 117, the second portion 133 of the L-shaped connector 129 moves proximally and distally within slot 135 in the wall of housing 112. The supply of injectable material 113 may include a syringe 111 that is in operable communication with L-shaped connector 129. In the illustrated embodiment syringe 111 is connected to L-shaped connector 129 through tubing 153 and 155. In other embodiments the end 157 of syringe 111 may be directly connected to L-shaped connector 129. The syringe 111 may be, for example, a plunger or screw type syringe. A shut off valve 161 may be located between tubing 153 and 155 to allow or stop flow of material from syringe 111 to device 110.

In one method of delivering injectable material to a treatment site, the shut off valve 161 can be used to create back pressure within syringe 111 that can be used to flow injectable material through device 110. For instance, the injector screw 159 of the injection syringe 111 can be turned to flow injectable material into the device 110 in order to prime the elongated injection member 128 with injectable material. The valve 161 can then be closed off to stop flow of injectable material into the elongated injection member 128. The deployment cannula 118 can be positioned within a treatment site and the distal end portion 142 of the elongated injection member 128 can be partially or fully advanced into the treatment site. With the valve 161 remaining in the closed position, the injector screw 159 can be turned to build up pressure within the syringe 111. The valve 161 may then be opened and the elongated injection member 118 can be advanced or retracted as the back pressure pushes a bolus of material injected under such pressure through the elongated injection member 128 and into the treatment site.

Figure 12:
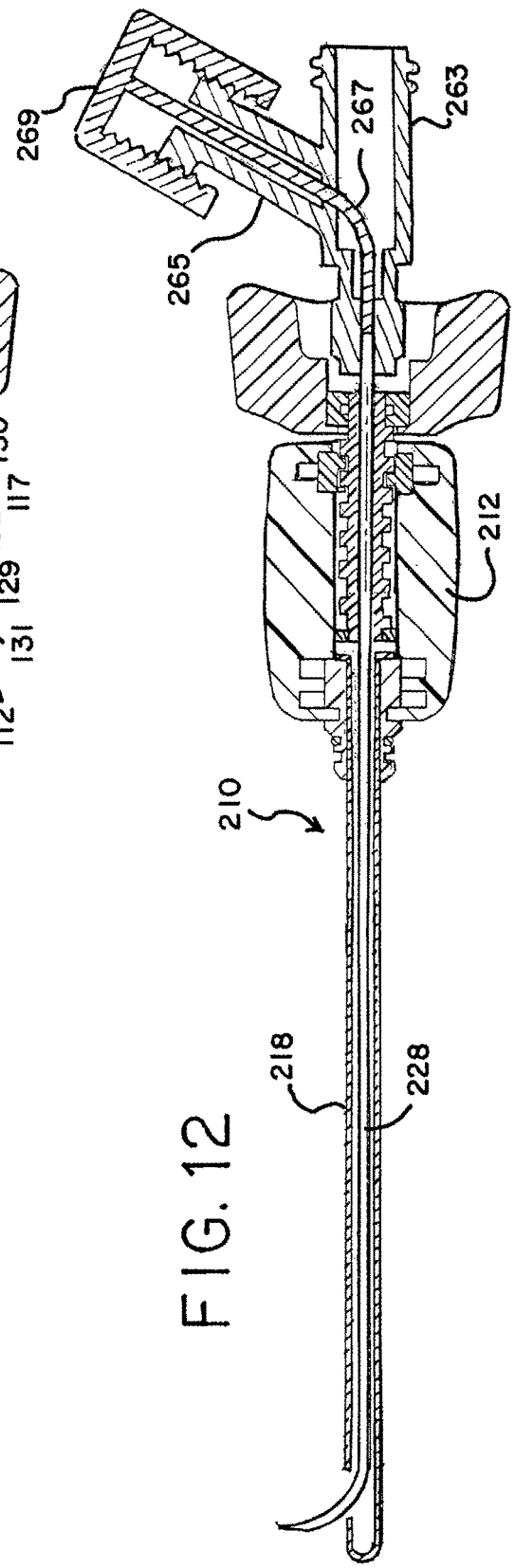
FIG. 12 is a cross-sectional view of another embodiment of a material delivery device in accordance with the present disclosure.

FIG. 12 illustrates another embodiment of an injection device 210 in accordance with the present disclosure. Injection device 210 has similar features to that of the previously described devices including having a housing 212, a deployment cannula 218 and an elongated injection member 228. In the embodiment of FIG. 12, the injectable material receiving port includes a Y-connector 264 having a first port 263 and a second port 265. The first and second ports 263 and 265 may both be used to receive injectable materials. Alternatively, the first or second ports 263 and 265 may receive a plunger or obturator 267 that is inserted into the lumen of the elongated injection member 228 to expel or remove clogs or unwanted materials therefrom. For example, the lumen of the elongated injection member 228 may become clogged with tissue or injectable material during use. When this happens, the plunger 267 may be inserted through the port 265 of the Y-connector 264 and into the lumen where the plunger contacts and breaks up the clog. The plunger 267 in FIG. 12 is not shown to size. The plunger 267 may have sufficient length to extend along the entire length of elongated injection member 228, partially along injection member 228 or out of the distal end portion of injection member 228. When injection member 228 serves or acts as a channel creation device or bone tamp, the plunger 267 may extend to and be substantially coextensive with the distal opening of injection member 228. The plunger 267 may be sufficiently flexible to be introduced through connector 264 and into the lumen of elongated injection member 228 but sufficiently rigid to unclog blockages within the lumen of elongated injection member 228. In the illustrated embodiment, the plunger 267 is connected to a screw on cap 269 that screws on to second port 265. Alternatively, plunger 267 may be insertion through the port 263 so as to optimize the column strength of an obturator through a straight path rather than a curved path. Furthermore, a plunger 267 may be employed with any of the embodiments described herein. In the injection device only includes a single port, the plunger and material source may be interchanged, as required by the particular application.

FIG. 12A illustrates another embodiment of a material delivery device 310 which includes several features similar to those of the material delivery devices described above, including shells 319a/319b that are attached to each other by screws 323 to form a housing, a deployment cannula 318, an elongated injection member 328, a drive member 330, a gripping member 360 and a material receiving port 364. In device 310, the torque limiting mechanism between the housing and the delivery cannula 318 has a different configuration than that described above. Additionally, device 310 includes a drive limiting mechanism associated with the drive member 330 that disconnects drive force to the drive member 330 if a threshold level of insertion resistance is encountered during distal advancement and insertion of the elongated injection member 328 into the treatment site. Such drive limiting mechanisms associated with the drive member may be incorporated into any of the material injection devices disclosed herein. Additionally, the configuration of the torque limiting mechanism between the housing and delivery cannula may also be incorporated into any of the material delivery devices disclosed herein.

Turning first to the drive limiting mechanism, such mechanism may be any suitable drive limiting mechanism that limits or discontinues transmission of drive force to the drive member. For example, the drive limiting mechanism may be a torque limiting mechanism, such as a shear pin, magnetic forces, friction fit, or ball and detent. FIG. 12A illustrates one example of drive limiting mechanism which includes a ball and detent torque limiting mechanism between gripping member 360 and drive member 330. The torque limiting mechanism limits or discontinues the transmission of drive force from gripping member 360 to drive member 330 when a threshold level of insertion resistance is encountered during insertion of the elongated material injection member 328 into the treatment site. The torque limiting mechanism reduces the risk of tissue injury and damage to the device when a threshold lever of insertion resistance is encountered.

The torque limiting mechanism includes a detent surface (such as a notch or recess) associated with either the gripping member 360 or the drive member 330 wherein a ball is biased into the detent. The mating between the ball and the detent normally transmits the rotational force from the gripping member 360 to the drive member 330 to rotate the drive member 330. In the embodiment illustrated in FIG. 12A, the proximal end portion 350 of drive member 330 includes a detent 380 on an outer surface thereof. The gripping member 360 includes a biasing member 382, such as a coiled spring, associated therewith. The biasing member 382 biases a ball 384 into detent 380. The engagement of ball 384 and detent 380 transmits rotational force from gripping member 360 to drive member 330 which advances elongated injection member 328 through deployment cannula 318 and into the treatment site. If the elongated injection member 328 encounters a certain threshold of resistance to insertion that exceeds the biasing force holding the ball 384 in the detent 380, the ball 384 slips out of the detent 380, and the gripping member 360 is allowed to continue to rotate while the drive member 330 remains stationary relative to the housing, thereby discontinuing advancement of the elongated injection member 328. The drive limiting mechanism is preferably reengageable so that the drive member 330 may be rotated in the opposite direction to retract the elongated injection member 328 from the treatment site. In the illustrated embodiment, the ball 384 is reengaged with the detent 380 by continued rotation of the gripping member 360 relative to the drive member 330 to realign the ball 384 with the detent 380. After reengagement of the drive limiting mechanism, the gripping member 360 may be rotated in the opposite direction to retract the drive member 330 proximally which results in retraction of the elongated injection member 328 from the treatment site.

Turning now to the torque limiting mechanism between the deployment cannula 328 and housing illustrated in FIG. 12A, the proximal end portion 334 of hub 332 includes a hollow cylinder or sleeve in which drive member 330 is disposed when the device 310 is assembled. The torque limiting mechanism is similar to that describe above and may be any suitable torque limiting mechanism that transmits rotational force between the housing and deployment cannula 328 until a threshold level of torque resistance is encountered. In the illustrated embodiment, the torque limiting mechanism is located between the cylindrical proximal end portion 334 and the housing. The torque limiting mechanism includes a detent surface (such as a notch or recess) located in either the proximal end portion 334 of the hub 32 or the housing, wherein a ball is biased into the detent. The mating between the ball and the detent normally transmits the rotational force from the housing to the hub 332 to rotate the delivery cannula 318 with the housing 12. In illustrated embodiment, the proximal portion 334 of hub 332 includes a detent 333 in a sidewall thereof. The housing includes a biasing member 339 associated therewith, such as a coiled spring, that biases a ball 341 into detent 333. Similar to the torque limiting mechanisms described above with respect to FIGS. 6-8, the housing may include a channel in an inner wall thereof wherein the biasing member 339 is disposed within the channel and biases ball 341 into detent 333. The engagement of ball 341 and detent 333 transmits rotational force from the housing to the hub 332. When the deployment cannula 318 encounters a certain threshold of rotational resistance that exceeds the biasing force holding the ball 341 in the detent 333, the ball slips out of the detent, and the housing is allowed to continue to rotate relative to the hub 332. Thus, the deployment cannula 318 remains stationary within the treatment site as the housing continues to rotate.

Also in this embodiment, the cylindrical proximal end portion of the hub 332 includes a proximal surface 331 that may contact nut 358 to hold nut 358 in position within the housing as the drive member 330 is rotated within the cylindrical proximal end portion 334 of hub 332 during advancement or retraction of the drive member 330.

Depending on the application, the features of the devices disclosed in FIGS. 1, 11, 12 and 12A may be combined with each other and/or combined with any other features disclosed herein.

Figure 13:
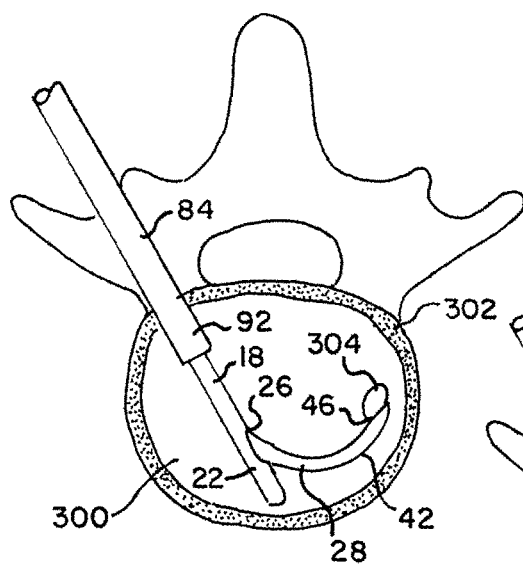
FIGS. 13-16 illustrate a method for treating a vertebral body in accordance with the present disclosure.
Figure 14:
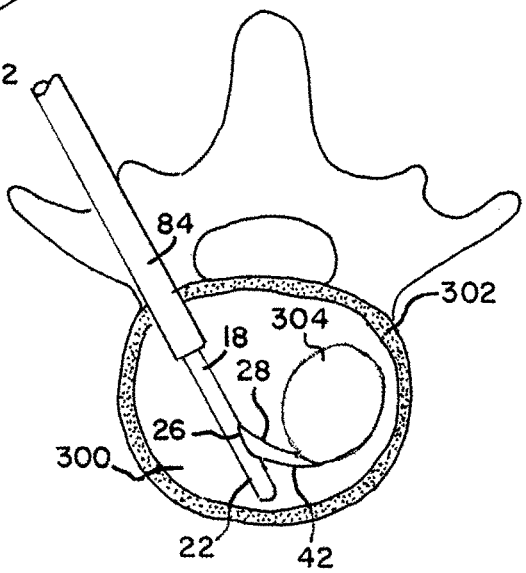
Figure 15:
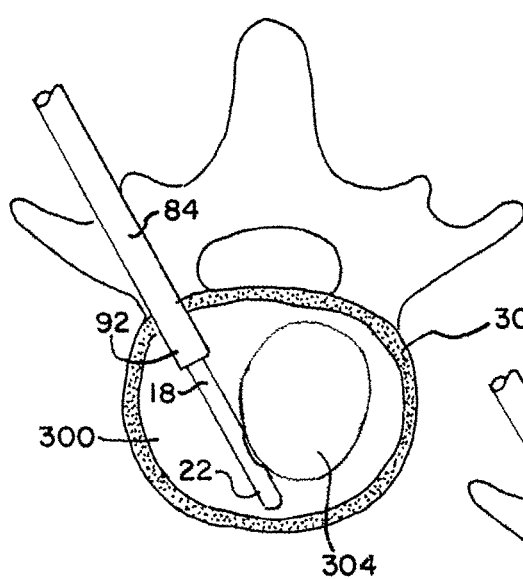

FIGS. 13-15 illustrate one embodiment of a method of treating a bone such as a vertebral body with the injection devices disclosed herein. Referring to FIG. 13, the distal end portion 92 of access cannula 84, optionally, may be inserted into the interior region 300 of a vertebral body 302. When the distal end tip 25 of deployment cannula 18 includes an introducer tip for insertion through tissue and into the treatment site, as illustrated in FIG. 4, an access cannula is not required. When an access cannula is present, the distal end portion 22 of the delivery cannula 18 of device 10 is inserted through the access cannula 84 and into the vertebral body 302. The operator may use, if present, any indicators included on the access cannula 84 and/or the device 10 to orient the distal end portion 22 of the delivery cannula 18 in the desired direction and to determine the trajectory of the distal end portion 42 of the elongated injection member 28 as it exits from the deployment cannula 18. Once the deployment cannula 18 is in the desired position within the treatment site, the elongated injection member 28 in a substantially linear configuration is advanced distally through the deployment cannula 18 and out of the opening 26 in the distal end thereof to form channels within the bone of the vertebral body and/or to position the elongated injection member 28 for injection of injectable material within the vertebral body.

As the distal end portion 42 of the elongated injection member 28 is advanced out of the distal end opening 26 of the deployment cannula 18, it inherently or by mechanical assistance curves into a generally arcuate configuration as described above. As also described above, the distal end portion 42 of the elongated injection member 28 may, optionally, include a Tuohy-Huber type tip and/or varying radii therealong to substantially reduce coring of the tissue by the distal opening 46 of the elongated injection member 28 as it is inserted into the treatment site. Alternatively or in combination with the Tuohy-Huber type tip or varying radii, an obturator may be present within lumen of the injection member 28, as described above with respect to FIG. 12, to prevent tissue or other debris from entering the injection member as it is inserted into the treatment site.

Depending on the application, injectable material 304 may be, optionally, injected into the treatment site through the elongated injection member 28 as the distal end portion 42 thereof exits the distal end portion 22 of the delivery cannula 18. Alternatively, the elongated injection member 28 may be used to create a channel within the tissue, such as cancellous bone tissue, and then the injectable material may be injected through the elongated injection member 28 into the channel and/or surrounding tissue after the distal end portion 22 has been retracted from the thus formed channel or as the distal end portion 22 is being retracted from the thus formed channel. If an obturator is used during insertion of the elongated injection member 28 into the tissue for channel creation or injecting injectable material, the obturator is removed from the elongated injection member 28 prior to injection of the injectable material.

Depending on the procedure the operator may desire to rotate deployment cannula 18 while the distal end portion 42 of the elongated injection member 28 is extended therefrom to "sweep" the elongated injection member 28 through tissue in the treatment site. In such procedures, the device 10 may include the above-described torque limiting mechanism between the housing and the deployment cannula 18 that discontinues transmission of rotational forces from the housing 12 to the deployment cannula 18 when a threshold level of rotational resistance is met.

Referring to FIG. 14, the elongated injection member 28 is retracted back into deployment cannula 18. As the elongated injection member 28 is retracted, the injectable material 304 may be, optionally, continually or intermittently injected through the elongated injection member 28 and into the treatment site. The elongated injection member 28 returns to the substantially linear configuration as it is retracted back into deployment cannula 18. In FIG. 15, the elongated injection member 28 has been fully retracted into the deployment cannula 18, leaving injectable material 304 within the vertebral body to reinforce the vertebral body against further fracture.

Figure 16:
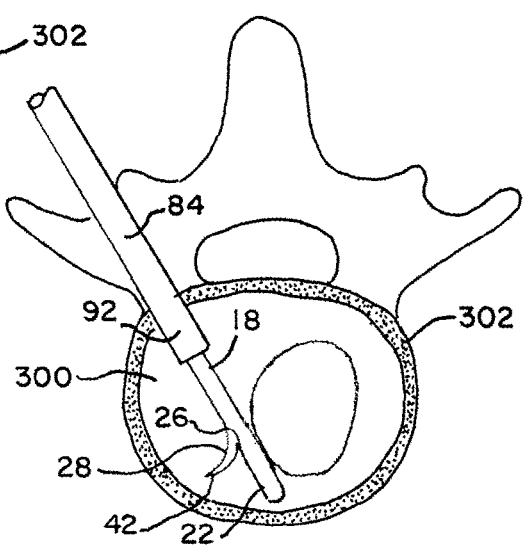

Turning to FIG. 16, if desired, the deployment cannula 18 may, after a first injection of material, be rotated a desired amount within access cannula 84 so that the elongated injection member 28 may be deployed in different directions. When present, indicators on the access cannula 84 and/or housing 12 of device 10 may be used to reposition the deployment cannula 18 in a desired orientation, after which injectable material may be injected into the treatment site as described above with regards to FIGS. 13-15. Repositioning and injecting material may be repeated as many times and in as many directions as desired for a given procedure.

In another embodiments, the elongated injection member 28 may be employed to first create multiple channels within the bone tissue by repositioning the elongated injection member in different orientations within the treatment site. After the desired number of channels has been created, the elongated injection is then used to injection injectable material into the multiple channels. As discussed above, if an obturator is located within the elongated injection member 28 during the creation of the channels, the obturator is removed from the elongated injection member 28 prior to injection of the injectable material.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A device for injecting material into a body, comprising:
   a housing having proximal and distal end portions;
   an elongated deployment cannula having a proximal end portion, a distal end portion and a longitudinal axis, the elongated deployment cannula also including a lumen extending axially within the cannula from an opening in the proximal end portion of the elongated deployment cannula to an opening in the distal end portion of the elongated deployment cannula, the proximal end portion of the elongated deployment cannula being operatively connected to the distal end portion of the housing, and the distal end portion of the elongated deployment cannula being configured for insertion into the body;
   a rotary drive member having a proximal end portion and a distal end portion with a threaded section extending axially therealong, the rotary drive member extending through a proximal end opening in the housing with the threaded section being at least partially disposed within the housing wherein the housing includes a corresponding threaded section in operative engagement with the threaded section of the rotary drive member and whereby rotational movement of the rotary drive member relative to the housing results in linear movement of the rotary drive member substantially along the longitudinal axis of the deployment cannula;
   an elongated injection member for injecting material into the body, the elongated injection member being disposed and moveable within the lumen of the deployment cannula, the elongated injection member having a proximal end portion, a distal end portion and a lumen extending between an opening in the proximal end portion of the elongated injection member and an opening in the distal end portion of the elongated injection member, the proximal end portion of the elongated injection member being rotatably connected to the rotary drive member such that when the rotary drive member is rotated relative to the housing, the elongated injection member does not rotate with the drive member and distal linear movement of the rotary drive member advances the elongated injection member distally through the lumen of the deployment cannula to extend the distal end portion of the elongated injection member out of the distal end portion opening of the deployment cannula; and a material inlet port in communication with the lumen of the elongated injection member and configured for connection to a material source, the rotary drive member being rotatable relative to the material inlet port.

2. The device of claim 1 wherein at least the distal end portion of the elongated injection member has a first generally linear configuration while disposed within the lumen of the deployment cannula.

3. The device of claim 2 wherein at least the distal end portion of the elongated injection member when extending out from the distal end portion opening of the deployment cannula has a second generally non-linear configuration.

4. The device of claim 3 wherein the second generally non-linear configuration comprises an arcuate configuration.

5. The device of claim 4 wherein the elongated injection member is generally cylindrically shaped tubular member and the distal end portion opening of the elongated injection member is defined by a substantially flat inclined surface at a distal tip of elongated injection member.

6. The device of claim 4 wherein the elongated injection member comprises a Tuohy-Huber needle.

7. The device of claim 4 wherein the arcuate configuration is defined by a plurality of differing radii of curvature.

8. The device of claim 7 wherein a proximal section of the distal end portion has a larger radius of curvature than a more distal section of the distal end portion.

9. The device of claim 1 wherein the proximal end portion of the elongated injection member extends through the rotary drive member.

10. The device of claim 1 further including an injectable material source coupled to the material inlet port.

11. The device of claim 1 wherein a grippable portion is located at the proximal end portion of the rotary drive member.

12. The device of claim 1 wherein the deployment cannula and the housing are rotatable relative to one another.

13. The device of claim 12 comprising a torque limiter operably connected between the deployment cannula and the housing.

14. The device of claim 13 in which the torque limiter includes a torque disconnect clutch that disconnects a transfer of torque from the housing to the deployment cannula when the torque reaches a selected threshold.

15. The device of claim 14 wherein the torque disconnect clutch comprises a detent associated with one of the deployment cannula and the housing and a biased detent-engaging member associated with the other of the deployment cannula and the housing, wherein the detent slips past the detent engaging member when the torque reaches the selected threshold.

16. The device of claim 1 wherein the housing and/or the deployment cannula includes a visual indicator indicating a trajectory of the distal end portion of the elongated injection member when the distal end portion of the elongated injection member extends from the distal end portion opening of the deployment cannula.

17. The device of claim 1 wherein a distal tip of the deployment cannula includes a tissue piercing member.

18. The device of claim 1 further including an access cannula adapted for insertion into the body, the deployment cannula being advanceable through the access cannula and into the body, and the access cannula having visual markers for aligning the position of the deployment cannula within the body.

19. The device of claim 1 further including a torque limiter associated with the rotary drive member, wherein the torque limiter discontinues drive forces to the drive member when a threshold of resistance is encountered.

* * * * *